United States Patent
Victors et al.

(10) Patent No.: US 10,146,914 B1
(45) Date of Patent: *Dec. 4, 2018

(54) SYSTEMS AND METHODS FOR EVALUATING WHETHER PERTURBATIONS DISCRIMINATE AN ON TARGET EFFECT

(71) Applicant: Recursion Pharmaceuticals, Inc., Salt Lake City, UT (US)

(72) Inventors: Mason L. Victors, Salt Lake City, UT (US); Blake C. Borgeson, Salt Lake City, UT (US); Cedric St-Jean-Leblanc, Montreal (CA)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/910,822

(22) Filed: Mar. 2, 2018

Related U.S. Application Data

(60) Provisional application No. 62/637,121, filed on Mar. 1, 2018.

(51) Int. Cl.
| | |
|---|---|
| G01N 33/48 | (2006.01) |
| G01N 33/50 | (2006.01) |
| G06F 19/00 | (2018.01) |
| G01N 21/64 | (2006.01) |
| G06F 19/18 | (2011.01) |
| G06F 17/18 | (2006.01) |

(52) U.S. Cl.
CPC ....... *G06F 19/706* (2013.01); *G01N 21/6428* (2013.01); *G01N 21/6458* (2013.01); *G06F 19/18* (2013.01); *G06F 17/18* (2013.01)

(58) Field of Classification Search
None
See application file for complete search history.

(56) References Cited

U.S. PATENT DOCUMENTS

| | | | |
|---|---|---|---|
| 2002/0052692 A1* | 5/2002 | Fahy | G06F 19/24 702/19 |
| 2017/0276686 A1 | 9/2017 | Marcotte et al. | |

OTHER PUBLICATIONS

Agarwal, N. et al., 2003, "RNA Interference: Biology, Mechanism, and Applications," Microbiol Mol Biol Rev. 67:657-685.
Basaji et al., 2007, "Cellular Image Analysis and Imaging by Flow Cytometry," Clin Lab Med 27, 653-670.
Beekhuizen et al., 2011, "Osteoarthritic synovial tissue inhibition of proteoglycan production in human osteoarthritic knee cartilage: establishment and characterization of a long-term cartilage-synovium coculture," Osteoarthritis 63, 1918-1927.
Bray et al., 2016, "Cell Painting, a high-content image-based assay for morphological profiling using multiplexed fluorescent dyes," Nature Protocols, 11, p. 1757-1774.
Buenrostro et al., 2013, "Transposition of native chromatin for fast and sensitive epigenomic profiling of open ahromatin, DNA-binding proteins and nucleosome position," Nature Methods 10, 1213-1218.
Buenrostro et al., 2015, "ATAC-seq: A Method for Assaying Chromatin Accessibility Genome-Wide," Current Protocols in Molecular Biology: 21.29.1-21.29.9.
Buggenthin et al., 2017, "Prospective identification of hematopoietic lineage choice by deep learning," Nature Methods, 14(4), 403-406.
Buul, 2012, Osteoarthritis and Cartilage 20, 1186-1196.
Carpenter et al., 2006, "CellProfiler: image analysis software for identifying and quantifying cell phenotypes," Genome Biol. 7, R100 PMID: 17076895.
Colas et al., 2000, "Targeted modification and transportation of cellular proteins," Proc. Natl. Acad. Sci. USA. 97 (25): 13720-13725.
Doyon, 2008, "Heritable targeted gene disruption in Zebrafish using designed zinc-finger nucleases," Nature Biotechnology 26, 702-708.
Gustafsdottir and Ljosa et al., 2013, PLOS Tenth Anniversary, https://doi.org/10.1371/journal.pone.0080999, accessed Nov. 19, 2017.
Heike and Nakahata, 2002, "Ex vivo expansion of hematopoietic stem cells by cytokines," Biochim Biophys Acta 1592, 313-321.
Huang et al., 2011, "MimoDB 2.0: a mimotope database and beyond," Nucleic Acids Research. 40(1): D271-D277.
Jones et al., 2008, CellProfiler Analyst: data exploration and analysis software for complex image-based screens, BMC Bioinformatics 9(1):482/doi: 10.1186/1471-2105-9-482. PMID: 19014601 PMCID: PMC261443.
Kamentsky et al., 2011, "Improved structure, function, and compatibility for CellProfiler: modular high-throughput image analysis software," Bioinformatics 2011/doi. PMID: 21349861 PMCID: PMC3072555.
Kay et al., 2017, "Mesenchymal Stem Cell-Conditioned Medium Reduces Disease Severity and Immune Responses in Inflammatory Arthritis," Nature 7, 18019.
Koos, 2015, "DIC image reconstruction using an energy minimization framework to visualize optical path length distribution," Sci. Rep. 6, 30420.

(Continued)

*Primary Examiner* — Russell S Negin
(74) *Attorney, Agent, or Firm* — Morgan Lewis & Bockius LLP

(57) ABSTRACT

Systems and methods for determining whether a set of test perturbations discriminates over a null distribution for an on target effect against a first component of an entity are disclosed. The perturbations are perturbations of the first component and the entity comprises a plurality of components. For each perturbation in the set, a corresponding vector comprising a plurality of elements, is obtained. Each element comprises a distribution metric of measurements of a feature across instances of the entity upon exposure to the respective perturbation or (ii) a distribution metric of a respective dimension reduction component computed using the measurement of the plurality of features across instances of the entity upon the perturbation exposure. A composite metric is computed, using the vectors, and compared to a null distribution. When the composite metric is differentiated from the null distribution, the set of perturbations is deemed to discriminate the on target effect against the first component over the null distribution.

28 Claims, 12 Drawing Sheets

(56) References Cited

OTHER PUBLICATIONS

Krutzik et al., 2008, "High-content single-cell drug screening with phospospecific flow cytometry," Nature Chemical Biology 4, 132-142.

Krutzik et al., 2011, "Fluorescent Cell Barcoding for Multiplex Flow Cytometry," Curr Protoc Cytom Chapter 6: Unit 6.31.

Kuhn, J. 2013, et al., "Label-free cytotoxicity screening assay by digital holographic microscopy," Assay Drug Dev. Technol. 11, 101-107.

Li et al., 2008, "IsoLasso: A LASSO Regression Approach to RNA-Seq Based Transcriptome Assembly," Cell 133, 523-536.

Maher et al., 2009, "Transcriptome sequencing to detect gene fusions in cancer," Nature. 458 (7234): 97-101.

Martin, 1981, "Isolation of a pluripotent cell line from early mouse embryos cultured in medium conditioned by teratocarcinoma stem cells," PNAS 78, 7634.

Newgard et al., 2009, "A branched-chain amino acid-related metabolic signature that differentiates obese and lean humans and contributes to insulin resistance," Cell Metab 9: 311-326, 2009.

Ni et al., 2011, "Nucleic acid aptamers: clinical applications and promising new horizons," Curr Med Chem 18(27), 4206.

Nilsen and Gravley, 2010, Expansion of the eukaryotic proteome by alternative splicing, 2010, Nature 463, 457-463.

Paddison et al., 2002, "Short hairpin RNAs (shRNAs) induce sequence-specific silencing in mammalian cells," Genes Dev. 16:948-958.

Rappaz et al., 2014 "Digital holographic microscopy: a quantitative label-free microscopy technique for phenotypic screening," Comb. Chem. High Throughput Screen 17, 80-88.

Reverdatto et al., 2015, "Peptide aptamers: development and applications," Curr. Top. Med. Chem. 15 (12): 1082-1101.

Sander and Young, 2014, "CRISPR-Cas systems for editing, regulating and targeting genomes," Nature Biotechnology 32, 347-355.

Sharma, 2013, "Metabolomics Reveals Signature of Mitochondrial Dysfunction in Diabetic Kidney Disease," J Am Soc Nephrol 24, 1901-12.

Singh et al., 2015, "Morphological profiles of RNAi-induced gene knockdown are highly reproducible but dominated by seed effects," PLoS One 10, e0131370.

Sui et al., 2002, A DNA vector-based RNAi technology to suppress gene expression in mammalian cells, Proc Natl Acad Sci U S A 99:5515-5520.

Taxman et al., 2006, "Criteria for effective design, construction, and gene knockdown by shRNA vectors," BMC Biotechnology 6:7 (2006).

Tran et al., 2003, Expressing functional siRNAs in mammalian cells using convergent transcription, BMC Biotechnol 3:21.

Wan et al., 2015, "Panorama of ancient metazoan macromolecular complexes," Nature 525, 339-344.

Wang, 2011, "RE: Metabolite profiles and the risk of developing diabetes," Nat Med 17: 448-453.

\* cited by examiner

436 (cont.)
440 (cont)
442

The distance is an angular distance, for example, computed as:

$$\frac{\sum_i^n A_i B_i}{\sqrt{\sum_{i=1}^n A_i^2} \sqrt{\sum_{i=1}^n B_i^2}}$$

where $A_i$ is a test element $i$ in the respective test vector, $B_i$ is the measure of central tendency of corresponding test element $i$ in the plurality of test elements across the plurality of test vectors other than the respective test vector, and $n$ is the number of elements in respective test vector.

444

The first process further comprises computing the composite test metric 212 as a distribution metric, such as a measure of central tendency, of the plurality of test similarity metrics 214.

446

The measure of central tendency of the plurality of test similarity metrics 214 is an arithmetic mean, weighted mean, midrange, midhinge, trimean, Winsorized mean, median, or mode of the plurality of test similarity metrics.

448

Compute a null distribution 216 comprising a plurality of composite control metrics 218. Each respective composite control metric 218 in the plurality of composite control metrics is computed by a second process comprising selecting a respective set of control perturbations 220 from a plurality of perturbations. Each control perturbation 222 in the respective set of control perturbations 220 is against a different component 224 in the plurality of components.

450

The plurality of composite control metrics 218 comprises 100 composite control metrics or 1000 control metrics, each composite control metric representing a different combination of control perturbations from the plurality of perturbations.

452

The respective set of control perturbations 220 consists of between 3 and 10 different control perturbations 222, between 5 and 15 different control perturbations 222, or between 3 and 300 different control perturbations 222.

Fig. 4D

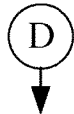

454

The second process further comprises obtaining, for each respective control perturbation 222 in the respective set of control perturbations 220, a corresponding control vector 226, thereby obtaining a respective plurality of control vectors. Each corresponding control vector 226 comprises a plurality of control elements 228. Each control element 228 in the plurality of control elements 228 comprises (i) a distribution metric of a measurement of a different feature, in the plurality of features, across a respective plurality of control instances 230 of the entity upon exposure of the respective plurality of control instances of the entity to the respective control perturbation 222 or (ii) a distribution metric of a respective dimension reduction component in a plurality of dimension reduction components computed using the measurement of the plurality of features across the respective plurality of control instances of the entity upon exposure of the respective plurality of control instances of the entity to the respective control perturbation.

456

The respective plurality of control instances 230 of the entity comprises 1000 control instances or 5000 control instances of the entity.

458

The exposure of the respective plurality of control instances 230 of the entity to the respective control perturbation 222 is for at least one hour or at least one day prior to obtaining the measurement.

460

The distribution metric of the measurement of the different feature across the plurality of control instances 230 of the entity upon exposure of the plurality of control instances 230 of the entity to the respective control perturbation 222 is an arithmetic mean, weighted mean, midrange, midhinge, trimean, Winsorized mean, median, or mode of the different feature across the plurality of control instances of the entity upon exposure of the plurality of control instances 230 of the entity to the respective control perturbation 222.

461

The distribution metric of the measurement of the different feature across the plurality of control instances 230 of the entity upon exposure of the plurality of control instances 230 of the entity to the respective control perturbation 222 is a measure of diversity (*e.g.*, range, standard deviation, variance, of the different feature across the plurality of control instances 230 of the entity upon exposure of the plurality of control instances 230 of the entity to the respective control perturbation 222.

Fig. 4E

|  | Feature 1 | Feature 2 | Feature 3 | ... | Feature N |
|---|---|---|---|---|---|
| Control perturbation 1 | | | | | |
| Control instance 1-1 | $p_{1\text{-}1\text{-}1}$ | $p_{1\text{-}1\text{-}2}$ | $p_{1\text{-}1\text{-}3}$ | ... | $p_{1\text{-}1\text{-}N}$ |
| Control instance 1-2 | $p_{1\text{-}2\text{-}1}$ | $p_{1\text{-}2\text{-}2}$ | $p_{1\text{-}2\text{-}3}$ | ... | $p_{1\text{-}2\text{-}N}$ |
| ... | ... | ... | ... | ... | ... |
| Control instance 1-Q | $p_{1\text{-}Q\text{-}1}$ | $p_{1\text{-}Q\text{-}2}$ | $p_{1\text{-}Q\text{-}3}$ | ... | $p_{1\text{-}Q\text{-}N}$ |
| Control perturbation 2 | | | | | |
| Control instance 2-1 | $p_{2\text{-}1\text{-}1}$ | $p_{2\text{-}1\text{-}2}$ | $p_{2\text{-}1\text{-}3}$ | ... | $p_{2\text{-}1\text{-}N}$ |
| Control cinstance 2-2 | $p_{2\text{-}2\text{-}1}$ | $p_{2\text{-}2\text{-}2}$ | $p_{2\text{-}2\text{-}3}$ | ... | $p_{2\text{-}2\text{-}N}$ |
| ... | ... | ... | ... | ... | ... |
| Control instance 2-Q | $p_{2\text{-}Q\text{-}1}$ | $p_{2\text{-}Q\text{-}2}$ | $p_{2\text{-}Q\text{-}3}$ | ... | $p_{2\text{-}Q\text{-}N}$ |
| Control perturbation M | | | | | |
| Control instance M-1 | $p_{M\text{-}1\text{-}1}$ | $p_{M\text{-}1\text{-}2}$ | $p_{M\text{-}1\text{-}3}$ | ... | $p_{M\text{-}1\text{-}N}$ |
| Control instance M-2 | $p_{M\text{-}2\text{-}1}$ | $p_{M\text{-}2\text{-}2}$ | $p_{M\text{-}2\text{-}3}$ | ... | $p_{M\text{-}2\text{-}N}$ |
| ... | ... | ... | ... | ... | ... |
| Control instance M-Q | $p_{M\text{-}Q\text{-}1}$ | $p_{M\text{-}Q\text{-}2}$ | $p_{M\text{-}Q\text{-}3}$ | ... | $p_{M\text{-}Q\text{-}N}$ |

Fig. 5

|  | Dimension reduction component 1 | Dimension reduction component 2 | Dimension reduction component 3 | ... | Dimension reduction component T |
|---|---|---|---|---|---|
| Test perturbation 206-1 | | | | | |
| Test instance 210-1-1 | $p_{1\text{-}1\text{-}1}$ | $p_{1\text{-}1\text{-}2}$ | $p_{1\text{-}1\text{-}3}$ | ... | $p_{1\text{-}1\text{-}N}$ |
| Test instance 210-1-2 | $p_{1\text{-}2\text{-}1}$ | $p_{1\text{-}2\text{-}2}$ | $p_{1\text{-}2\text{-}3}$ | ... | $p_{1\text{-}2\text{-}N}$ |
| ... | ... | ... | ... | ... | ... |
| Test instance 210-1-Q | $p_{1\text{-}Q\text{-}1}$ | $p_{1\text{-}Q\text{-}2}$ | $p_{1\text{-}Q\text{-}3}$ | ... | $p_{1\text{-}T\text{-}N}$ |
| Test perturbation 206-2 | | | | | |
| Test instance 210-2-1 | $p_{2\text{-}1\text{-}1}$ | $p_{2\text{-}1\text{-}2}$ | $p_{2\text{-}1\text{-}3}$ | ... | $p_{2\text{-}1\text{-}N}$ |
| Test instance 210-2-2 | $p_{2\text{-}2\text{-}1}$ | $p_{2\text{-}2\text{-}2}$ | $p_{2\text{-}2\text{-}3}$ | ... | $p_{2\text{-}2\text{-}N}$ |
| ... | ... | ... | ... | ... | ... |
| Test instance 210-2-Q | $p_{2\text{-}Q\text{-}1}$ | $p_{2\text{-}Q\text{-}2}$ | $p_{2\text{-}Q\text{-}3}$ | ... | $p_{2\text{-}T\text{-}N}$ |
| Test perturbation 206-M | | | | | |
| Test instance 210-M-1 | $p_{M\text{-}1\text{-}1}$ | $p_{M\text{-}1\text{-}2}$ | $p_{M\text{-}1\text{-}3}$ | ... | $p_{M\text{-}1\text{-}N}$ |
| Test instance 210-M-2 | $p_{M\text{-}2\text{-}1}$ | $p_{M\text{-}2\text{-}2}$ | $p_{M\text{-}2\text{-}3}$ | ... | $p_{M\text{-}2\text{-}N}$ |
| ... | ... | ... | ... | ... | ... |
| Test instance 210-M-Q | $p_{M\text{-}Q\text{-}1}$ | $p_{M\text{-}Q\text{-}2}$ | $p_{M\text{-}Q\text{-}3}$ | ... | $p_{M\text{-}T\text{-}N}$ |

Fig. 6

SYSTEMS AND METHODS FOR EVALUATING WHETHER PERTURBATIONS DISCRIMINATE AN ON TARGET EFFECT

CROSS REFERENCE TO RELATED APPLICATIONS

This application claims priority to U.S. Patent Application No. 62/637,121, entitled "SYSTEMS AND METHODS FOR EVALUATING WHETHER PERTURBATIONS DISCRIMINATE AN ON TARGET EFFECT," filed Mar. 1, 2018, which is hereby incorporated by reference.

TECHNICAL FIELD

The present disclosure relates generally to systems and methods for identifying a set of perturbations that have an on target effect against a selected target.

BACKGROUND

Many diseases present with specific structural phenotypes, as with the distinct facial features of patients with Cornelia de Lange Syndrome. Similarly, specific structural signatures for many diseases are accessible via cellular images. As such, automated microscopic imaging provides a suitable basis for a high throughput screening platform to study these specific cellular structural signatures. Microscopic imaging provides information on functional data points together with associated spatial information in x, y and z dimensions.

Microscopic imaging techniques have advanced over the past few years. Advances in optics, robotics and computational techniques, as well as an expanding repertoire of contrast markers, including functional live-cell reporters, are contributing to the widespread adoption of image-based screening platforms that provide highly dynamic and quantitative fluorescence readouts in cell-based assay systems. See Bickle, 2010, "The beautiful cell: high-content screening in drug discovery," Anal. Bioanal Chem. 398, 219-226; Isherwood et al., 2011, "Live cell in vitro and in vivo imaging applications: accelerating drug discovery," Pharmaceutics 3, 141-170 (2011); and Kummel et al., 2010, "Integration of multiple readouts into the z' factor for assay quality assessment," J. Biomol. Screen 15, 95-101.

Non-invasive, label-free imaging techniques have recently emerged, fulfilling the requirements of minimal cell manipulation for cell-based assays in a high-content screening context. Among these label-free techniques, digital holographic microscopy (Rappaz et al., 2015 Automated multi-parameter measurement of cardiomyocytes dynamics with digital holographic microscopy," Opt. Express 23, 13333-13347) provides quantitative information that is automated for end-point and time-lapse imaging using 96- and 384-well plates. See, for example, Kuhn, J. 2013, et al., "Label-free cytotoxicity screening assay by digital holographic microscopy," Assay Drug Dev. Technol. 11, 101-107; Rappaz et al., 2014 "Digital holographic microscopy: a quantitative label-free microscopy technique for phenotypic screening," Comb. Chem. High Throughput Screen 17, 80-88; and Rappaz et al., 2015 in Label-Free Biosensor Methods in Drug Discovery (ed. Fang, Y.) 307-325, Springer Science+Business Media). Similarly, label-free optical techniques such as phase contrast or differential interference contrast (DIC) can be digitally reconstructed and quantified. See Koos, 2015, "DIC image reconstruction using an energy minimization framework to visualize optical path length distribution," Sci. Rep. 6, 30420. Light sheet fluorescence microscopy (LSFM) holds promise for the analysis of large numbers of samples, in 3D high resolution and with fast recording speed and minimal photo-induced cell damage. LSFM has gained increasing popularity in various research areas, including neuroscience, plant and developmental biology, toxicology and drug discovery, although it is not yet adapted to an automated HTS setting. See, Pampaloni et al., 2014, "Tissue-culture light sheet fluorescence microscopy (TC-LSFM) allows long-term imaging of three-dimensional cell cultures under controlled conditions," Integr. Biol. (Camb.) 6, 988-998; Swoger et al., 2014, "Imaging cellular spheroids with a single (selective) plane illumination microscope," Cold Spring Harb. Protoc., 106-113; and Pampaloni et al., 2013, "High-resolution deep imaging of live cellular spheroids with light-sheet-based fluorescence microscopy," Cell Tissue Res. 352, 161-177.

Cell Painting and related variants of cell painting represent another form of imaging technique that holds promise. Cell painting is a morphological profiling assay that multiplexes six fluorescent dyes, imaged in five channels, to reveal eight broadly relevant cellular components or organelles. Cells are plated in multiwell plates, perturbed with the treatments to be tested, stained, fixed, and imaged on a high-throughput microscope. Next, automated image analysis software identifies individual cells and measures any number between one and tens of thousands (but most often approximately 1,000) morphological features (various measures of size, shape, texture, intensity, etc. of various whole-cell and sub-cellular components) to produce a profile that is suitable for the detection of even subtle phenotypes. Profiles of cell populations treated with different experimental perturbations can be compared to suit many goals, such as identifying the phenotypic impact of chemical or genetic perturbations, grouping compounds and/or genes into functional pathways, and identifying signatures of disease. See, Bray et al., 2016, Nature Protocols 11, 1757-1774.

Microscopic imaging allows for high throughput screening in which cells are perturbed with a perturbation, such as an siRNA that is designed to disrupt a single gene within the cell while minimizing disruption of other genes, and the microscopic imaging is used to quantify the effects of such perturbations. In fact, such screening can be used to first identify a perturbation that causes cells to have the characteristics of a disease of interest, and further used to determine which compounds rescue the disease-associated characteristics induced by virtue of the perturbation. A drawback of known imaging techniques for such high throughput screening efforts is that they are expensive, inefficient and/or lack sufficient throughput potential.

A drawback that arises in known screening techniques, including cell painting, is that the magnitude and prevalence of off target effects cause the morphological profiles of perturbations targeting the same gene to look more dissimilar than those targeting different genes. See Singh et al., 2015, "Morphological profiles of RNAi-induced gene knockdown are highly reproducible but dominated by seed effects," PLoS One 10, e0131370. This phenomenon has been observed in other multiparametric assays, and it is not specific to morphological profiling using imaging techniques. This effect impedes large-scale experiments using perturbations such as short RNAi reagents, or any other perturbation with significant off target effects, in which the experimental design requires widespread comparisons across all samples.

Given the above background, what is needed in the art are systems and methods for compensating for off target effects in order to identify a set of perturbations that have an on target effect against a selected target.

SUMMARY

The present disclosure addresses the need in the art for systems and methods along with an ancillary set of perturbations, that allow the assessment and characterization of on target effects of imperfect perturbations such as siRNA. The present disclosure addresses techniques for drug discovery for any disease in which the reagents are of sufficiently non-specificity so as to require such an intervention to determine the on target effect. With respect to genetic diseases, several perturbations, such as siRNAs are used to model the human disease state. Several different perturbations are used for every gene. Similarly, several secreted factors or proteins (such as cytokines) could be used from multiple manufacturers so as to identify the on target nature of the protein in biology, and not a side-effect related to unique production or other unidentified causes of noise. A first goal is to identify a perturbation that disrupts the function of the gene that causes the disease under study, which is termed an "on target effect." Unfortunately, such perturbations have off target effects as well, in which the function of genes other than the genes responsible for a disease under study are perturbed as well. Advantageously, the systems and methods of the present disclosure address these off target effects. In the present disclosure, images of healthy cells are captured, upon exposure with several different perturbations (e.g., siRNAs) for a given gene. In the present disclosure, a determination is made as to the common phenotypic effects across the perturbations of a particular gene on the premise that such common phenotypic effects across the perturbations of the particular gene in fact represent the on target effects associated with disrupting the gene of interest. For instance, in the case where each perturbation is an siRNA, because each siRNA in the plurality of siRNAs is designed to disrupt a target gene, the common effect arising from such siRNA represents the on target effect of disrupting the gene among independent, and noisy, other off target effects caused by each of the individual siRNA. As such, in the present disclosure what is sought is a signal in common to the plurality of siRNA. Moreover, the present disclosure provides ways to screen for compounds that can reverse the on target effects of siRNA.

Thus, in the present disclosure a high dimensional phenotypic vector is obtained from cells that have been exposed to perturbations that target one or more genes associated with a target disease. Each such vector comprises a plurality of elements. Each such element represents a distribution metric of a measurement of a different feature, in a plurality of features, across a plurality of test instances of the cells or (ii) a distribution metric of a respective dimension reduction component in a plurality of dimension reduction components computed using the measurement of the plurality of features across a plurality of test instances of the cells. The high dimensional phenotypic string measured for each of these perturbations are compared to each other in order to identify a common signal, the on target signal. From this comparison, a particular perturbation (e.g., a particular siRNA) that is most representative of effects exhibited by the perturbations, (e.g. most representative of the high dimensional phenotypic string obtained from cells that have each been exposed to one of the perturbations that target the one or more genes) is selected as the target perturbation. The target perturbation forms the basis for high-throughput screening in which cells exposed to the target perturbation are used as the basis of a screening assay that seeks to identify compounds that, when exposed to the perturbation exposed cells, are able to reverse the on target effects exhibited by such perturbation exposed cells.

Accordingly, one aspect of the present disclosure provides systems and methods for determining whether a set of test perturbations discriminate (e.g., differentiate) over a null distribution formed using sets of control perturbations for an on target effect against a first component (e.g., gene) of an entity (e.g. cell). The set of test perturbations are perturbations of the first component and the entity comprises a plurality of components (e.g., a plurality of genes). For each perturbation in the set of test perturbations, a corresponding vector (e.g., high dimensional phenotypic string) comprising a plurality of elements, is obtained. Each element comprises a distribution metric of measurements of a feature across instances of the entity upon exposure to the respective perturbation or (ii) a distribution metric of a respective dimension reduction component computed using the measurement of the plurality of features across instances of the entity upon the perturbation exposure. A composite metric is computed, using the vectors described above, and compared to a null distribution. When the composite metric is differentiated from the null distribution, the set of perturbations is deemed to discriminate the on target effect against the first component relative to a null distribution formed using sets of control perturbations.

In more detail, one aspect of the present disclosure provides a computer system for determining whether a set of test perturbations discriminate over a null distribution, formed using sets of control perturbations, for an on target effect against a first component of an entity. The set of test perturbations comprises a plurality of test perturbations of the first component and the entity comprises a plurality of components including the first component. The computer system comprises one or more processors, a memory, and one or more programs. The one or more programs are stored in the memory and are configured to be executed by the one or more processors.

The one or more programs include instructions for obtaining, for each respective test perturbation in the set of test perturbations, a corresponding test vector, thereby obtaining a plurality of test vectors. Each corresponding test vector comprises a plurality of test elements. Each test element in the plurality of test elements comprises (i) a distribution metric of a measurement of a different feature, in a plurality of features, across a plurality of test instances of the entity upon exposure of the plurality of test instances of the entity to the respective test perturbation or (ii) a distribution metric of a respective dimension reduction component in a plurality of dimension reduction components computed using the measurement of the plurality of features across a plurality of test instances of the entity upon exposure of the plurality of test instances of the entity to the respective test perturbation.

The one or more programs further include instructions for computing a composite test metric, using the plurality of test vectors. The composite test metric quantifies the on target effect of the set of test perturbations against the first component. The test metric is computed by a first process. In the first process, for each respective test vector in the plurality of test vectors, a test similarly metric is computed between (i) the respective test vector and (ii) a distribution metric of the plurality of test vectors with the respective test vector removed from the plurality of test vectors, thereby obtaining a plurality of test similarity metrics for the plurality of test vectors. Each test similarity metric in the plurality of test similarity metrics uniquely corresponds to a perturbation in the first set of perturbations. The composite test metric is computed as a measure of central tendency of the plurality of test similarity metrics. A null distribution is computed. The null distribution comprises a plurality of composite control metrics, each respective composite control metric in the plurality of composite control metrics computed by a second process.

In the second process, a respective set of control perturbations is selected from the plurality of perturbations. Each control perturbation in the respective set of control perturbations is against a different component (e.g., gene) in the plurality of components. In the second process there is obtained, for each respective control perturbation in the respective set of control perturbations, a corresponding control vector, thereby obtaining a respective plurality of control vectors. Each corresponding control vector comprises a plurality of control elements. Each control element in the plurality of control elements comprises (i) a distribution metric of a measurement of a different feature, in the plurality of features, across a respective plurality of control instances of the entity upon exposure of the respective plurality of control instances of the entity to the respective control perturbation or (ii) a distribution metric of a respective dimension reduction component in a plurality of dimension reduction components computed using the measurement of the plurality of features across the respective plurality of control instances of the entity upon exposure of the respective plurality of control instances of the entity to the respective control perturbation. In the second process the respective composite control metric is computed, using the respective plurality of control vectors. The respective control metric quantifies the on target effect of the respective set of control perturbations against the corresponding different component.

The control metric is computed by a third process. In the third process, (1) for each respective control vector, a control similarity metric is computed between (i) the respective control vector and (ii) a distribution metric of the respective plurality of control vectors with the respective control vector removed from the respective plurality of control vectors, thereby obtaining a plurality of control similarity metrics for the respective plurality of control vectors. Each control similarity metric in the plurality of control similarity metrics uniquely corresponds to a perturbation in the respective set of control perturbations. The respective composite control metric is computed as a distribution metric of the plurality of control similarity metrics.

The one or more programs further include instructions for comparing the test metric to the null distribution. When the test metric is differentiated from the null distribution, the set of test perturbations is deemed to discriminate the on target effect against the first component relative to the null distribution formed using sets of control perturbations.

In some embodiments, each different feature is selected from a plurality of features, and each feature in the plurality of features represents a color, texture, or size of the entity or an enumerated portion of the entity upon exposure of the entity to the respective test perturbation or control perturbation.

In some embodiments, the distribution metric of the measurement of the different feature across the plurality of test instances of the entity upon exposure of the plurality of test instances of the entity to the respective test perturbation is an arithmetic mean, weighted mean, midrange, midhinge, trimean, Winsorized mean, median, or mode of the different feature across the plurality of test instances of the entity upon exposure of the plurality of test instances of the entity to the respective test perturbation.

In some embodiments, the distribution metric of the measurement of the different feature across the plurality of control instances of the entity upon exposure of the plurality of control instances of the entity to the respective control perturbation is an arithmetic mean, weighted mean, midrange, midhinge, trimean, Winsorized mean, median, or mode of the different feature across the plurality of control instances of the entity upon exposure of the plurality of control instances of the entity to the respective control perturbation.

In some embodiments, the set of test perturbations consists of between 2 and 12 different test perturbations. In some embodiments, the set of test perturbations consists of between 5 and 15 different test perturbations. In some embodiments, the set of test perturbations consists of between 3 and 300 different test perturbations.

In some embodiments, each test perturbation in the set of test perturbations further has an off target effect against one or more components in the plurality of components other than the first component.

In some embodiments, the plurality of test instances of the entity comprises 500 test instances of the entity. In some embodiments, the plurality of test instances of the entity comprises 5000 test instances of the entity.

In some embodiments, the exposure of the plurality of test instances of the entity to the respective test perturbation is for at least one hour or at least one day prior to obtaining the measurement.

In some embodiments, the plurality of test elements consists of between 5 test elements and 10,000 test elements. In some embodiments, the plurality of test elements consists of between 100 test elements and 2000 test elements.

In some embodiments, the measure of central tendency of the plurality of test vectors with the respective test vector removed from the plurality of test vectors is a measure of central tendency of each corresponding test element in the plurality of test elements across the plurality of test vectors other than the respective test vector.

In some embodiments, the test similarly metric between (i) the respective test vector and (ii) the distribution metric of the plurality of test vectors with the respective test vector removed from the plurality of test vectors is computed as a distance between corresponding elements of the test vector and the distribution metric of the plurality of test vectors with the respective test vector removed from the plurality of test vectors. In some such embodiments, distance is an angular distance. For instance, in some such embodiments, the angular distance is computed as:

$$\frac{\sum_{i}^{n} A_i B_i}{\sqrt{\sum_{i=1}^{n} A_i^2} \sqrt{\sum_{i=1}^{n} B_i^2}}$$

where $A_i$ is a test element i in the respective test vector, $B_i$ is the distribution metric of corresponding test element i in the plurality of test elements across the plurality of test vectors other than the respective test vector, and n is the number of elements in respective test vector.

In some embodiments, the measure of central tendency of the plurality of test similarity metrics is an arithmetic mean, weighted mean, midrange, midhinge, trimean, Winsorized mean, median, or mode of the plurality of test similarity metrics.

In some embodiments, the plurality of composite control metrics comprises 100 composite control metrics, and each composite control metric representing a different combination of control perturbations from the plurality of perturbations. In some embodiments, the plurality of composite control metrics comprises 1000 composite control metrics, and each composite control metric represent a different combination of control perturbations from the plurality of perturbations.

In some embodiments, the respective set of control perturbations consists of between 3 and 10 different control perturbations, between 5 and 15 different control perturbations, between 3 and 300 different control perturbations. In some embodiments, the respective plurality of control instances of the entity comprises 1000 control instances of the entity or comprises 5000 control instances of the entity.

In some embodiments, the exposure of the respective plurality of control instances of the entity to the respective control perturbation is for at least one hour or at least one day prior to obtaining the measurement.

In some embodiments, the plurality of test elements consists of between 5 test elements and 10,000 test elements, the plurality of control elements consists of between 5 control elements and 10,000 control elements, and there is a one to one correspondence between each test element in the plurality of test elements and a corresponding control element in the plurality of control elements.

In some embodiments, the plurality of test elements consists of between 100 test elements and 2000 test elements, the plurality of control elements consists of between 100 control elements and 2000 control elements, and there is a one to one correspondence between each test element in the plurality of test elements and a corresponding control element in the plurality of control elements.

In some embodiments, the measure of central tendency of the plurality of control vectors with the respective control vector removed from the respective plurality of control vectors is a measure of central tendency of each corresponding control element in the respective plurality of control elements across the respective plurality of control vectors other than the respective control vector. In some such embodiments, the control similarly metric between (i) the respective control vector and (ii) the measure of central tendency of the respectively plurality of control vectors with the respective control vector removed from the respective plurality of control vectors is computed as a distance between corresponding elements of the respective control vector and the measure of central tendency of the respective plurality of control vectors with the respective control vector removed from the respective plurality of control vectors. In some such embodiments, the distance is an angular distance, for instance, computed as:

$$\frac{\sum_{i}^{n} A_i B_i}{\sqrt{\sum_{i=1}^{n} A_i^2} \sqrt{\sum_{i=1}^{n} B_i^2}}$$

where $A_i$ is a control element i in the respective control vector, $B_i$ is the measure of central tendency of corresponding control element i in the plurality of control elements across the respective plurality of control vectors other than the respective control vector, and n is the number of elements in respective control vector.

In some embodiments, the measure of central tendency of the plurality of control similarity metrics is an arithmetic mean, weighted mean, midrange, midhinge, trimean, Winsorized mean, median, or mode of the plurality of control similarity metrics.

In some embodiments, the comparison of the test metric to the null distribution comprises using the null distribution to compute a Z-score for the test metric, where, when the test metric has a Z-score that exceeds a threshold value (e.g. 2.5, 6, etc.), the test metric is deemed to be differentiated from the null distribution.

In some embodiments, each dimension reduction component in the plurality of dimension reduction components is a principal component derived by principal component analysis.

In some embodiments, each feature in the plurality of features is an optical feature that is optically measured.

In some embodiments, a first subset of the plurality of features are optical features that are optically measured and a second subset of the plurality of features are non-optical features.

In some embodiments, each feature in the plurality of features is a feature that is non-optically measured.

In some embodiments, the different feature in the plurality of different features is measured individually for each test instance in the plurality of test instances of the entity.

In some embodiments, the different feature in the plurality of different features is measured across at least a subset of test instances in the plurality of test instances of the entity.

In some embodiments, the distribution metric of the measurement of the different feature across the plurality of test instances of the entity upon exposure of the plurality of test instances of the entity to the respective test perturbation is a measure of diversity (e.g., range, standard deviation, or variance) of the different feature across the plurality of test instances of the entity upon exposure of the plurality of test instances of the entity to the respective test perturbation.

In some embodiments, the distribution metric of the measurement of the different feature across the plurality of control instances of the entity upon exposure of the plurality of control instances of the entity to the respective control perturbation is a measure of diversity (e.g., range, standard deviation, or variance) of the different feature across the plurality of control instances of the entity upon exposure of the plurality of control instances of the entity to the respective control perturbation.

Another aspect of the present disclosure provides a method for determining whether a set of test perturbations discriminate (e.g., differentiate) over a null distribution, formed using sets of control perturbations, for an on target effect against a first component (e.g., gene) of an entity (e.g., cell). The set of test perturbations comprises a plurality of test perturbations of the first component and the entity comprises a plurality of components including the first component. The method comprises obtaining, for each respective test perturbation in the set of test perturbations, a corresponding test vector, thereby obtaining a plurality of test vectors. Each corresponding test vector comprises a plurality of test elements. Each element in the plurality of test elements comprises (i) a distribution metric of a measurement of a different feature, in a plurality of features, across a plurality of test instances of the entity upon exposure of the plurality of test instances of the entity to the respective test perturbation or (ii) a distribution metric of a respective dimension reduction component in a plurality of dimension reduction components computed using the measurement of the plurality of features across a plurality of test instances of the entity upon exposure of the plurality of test instances of the entity to the respective test perturbation. In the method a composite test metric is computed, using the plurality of test vectors described above. The composite test metric quantifies the on target effect of the set of test perturbations against the first component.

The test metric is computed by a first process comprising for each respective test vector in the plurality of test vectors, computing a test similarly metric between (i) the respective test vector and (ii) a measure of central tendency of the plurality of test vectors with the respective test vector removed from the plurality of test vectors, thereby obtaining a plurality of test similarity metrics for the plurality of test vectors, each test similarity metric in the plurality of test similarity metrics uniquely corresponding to a perturbation in the first set of perturbations. The first process further comprises computing the composite test metric as a distribution metric, such as a measure of central tendency (arithmetic mean, weighted mean, midrange, midhinge, trimean, Winsorized mean, median, or mode), of the plurality of test similarity metrics.

In the method a null distribution is computed. The null distribution comprises a plurality of composite control metrics. Each respective composite control metric in the plurality of composite control metrics is computed by a second process comprising selecting a respective set of control perturbations from a plurality of perturbations, where each control perturbation in the respective set of control perturbations is against a different component in the plurality of components. The second process further comprises obtaining, for each respective control perturbation in the respective set of control perturbations, a corresponding control vector, thereby obtaining a respective plurality of control vectors. Each corresponding control vector comprises a plurality of control elements. Each control element in the plurality of control elements comprising (i) a distribution metric of a measurement of a different feature, in the plurality of features, across a respective plurality of control instances of the entity upon exposure of the respective plurality of control instances of the entity to the respective control perturbation or (ii) a distribution metric of a respective dimension reduction component in a plurality of dimension reduction components computed using the measurement of the plurality of features across the respective plurality of control instances of the entity upon exposure of the respective plurality of control instances of the entity to the respective control perturbation. The second process further comprises computing the respective composite control metric, using the respective plurality of control vectors. The respective control metric quantifies the on target effect of the respective set of control perturbations against the corresponding different component.

The control metric is computed by a third process comprising, for each respective control vector, computing a control similarity metric between (i) the respective control vector and (ii) a measure of central tendency of the respective plurality of control vectors with the respective control vector removed from the respective plurality of control vectors, thereby obtaining a plurality of control similarity metrics for the respective plurality of control vectors, each control similarity metric in the plurality of control similarity metrics uniquely corresponding to a perturbation in the respective set of control perturbations. The third process further comprises computing the respective composite control metric as a measure of central tendency of the plurality of control similarity metrics.

The method further comprises comparing the test metric to the null distribution. When the test metric is differentiated from the null distribution, the set of test perturbations is deemed to have an on target effect against the first component.

Another aspect of the present disclosure provides a non-transitory computer readable storage medium and one or more computer programs embedded therein for determining whether a set of test perturbations has an on target effect against a first component of an entity, where set of test perturbations comprises a plurality of test perturbations of the first component and the entity comprises a plurality of components including the first component. The one or more computer programs comprise instructions which, when executed by a computer system, cause the computer system to perform any of the methods provided in the present disclosure.

BRIEF DESCRIPTION OF THE DRAWINGS

FIGS. 4A, 4B, 4C, 4D, 4E, 4F, and 4G collectively provide a flow chart of processes and features for determining whether a set of test perturbations discriminate (e.g., differentiate) over a null distribution, formed using sets of control perturbations, for an on target effect against a first component of an entity, where optional elements of the flow chart are indicated by dashed boxes, in accordance with various embodiments of the present disclosure.

FIG. 5 illustrates how measured features for a given test perturbation forms a test vector of observations with N elements, for each test perturbation in a set of test perturbations and the collective set of vectors of dimension N can be subjected to a feature reduction technique to derive a set of dimension reduction components based on observed variation of individual elements in the N-dimensional vectors across the dataset, in accordance with an embodiment of the present disclosure.

FIG. 6 illustrates how the test vectors of length N of FIG. 5 have been reduced to a plurality of vectors of length T, where T is a positive integer less than N, in accordance with an embodiment of the present disclosure.

Like reference numerals refer to corresponding parts throughout the several views of the drawings.

DETAILED DESCRIPTION

Figure 1:
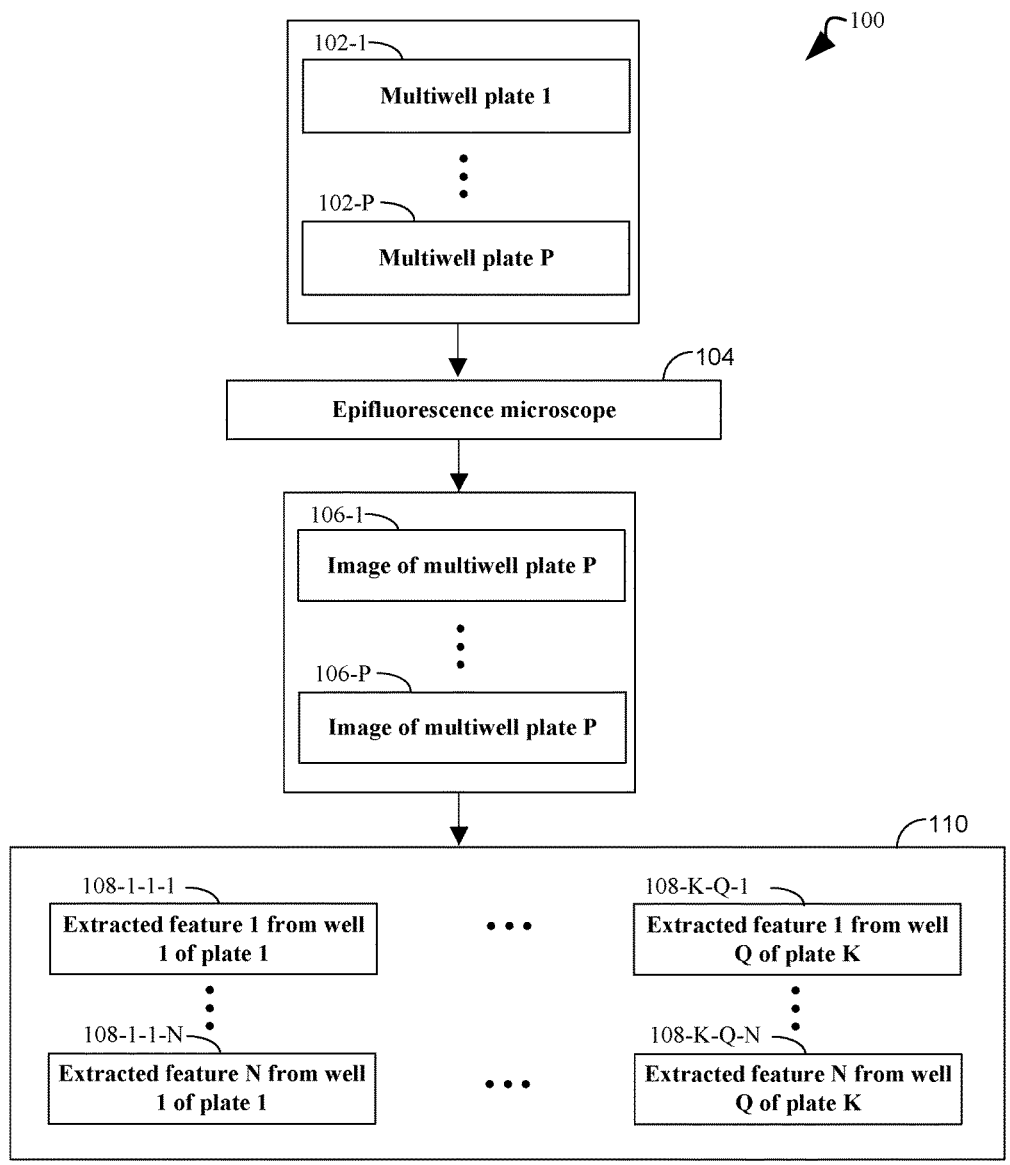
FIG. 1 illustrates an exemplary workflow for determining whether a set of test perturbations discriminate (e.g., differentiate) over a null distribution, formed using sets of control perturbations, for an on target effect against a first component of an entity, where the set of test perturbations comprises a plurality of test perturbations of the first component and the entity comprises a plurality of components including the first component, in accordance with an embodiment of the present disclosure.

Referring to FIG. 1, the present disclosure relies upon the acquisition of a data set 110 that comprises measurements of a plurality of features 108. Instances of an entity are plated into each well of multiwell plates 102 and exposed to perturbations. As an example, instances of cells are exposed to siRNA that target specific genes in the cells. For each entity that is exposed to a perturbation, the plurality of features is measured, thereby forming the data set. In practice, this is accomplished by capturing images 106 of the multiwell plates using, for example, an epifluorescence microscope. The images 106 are then used as a basis for extracting several different features from each of the wells in the multiwell plates thereby forming the dataset 110. The data set 110 is used to determine the on target effect against a particular component of the entity. For instance, the data set 110 is used to determine the on target effect each siRNA in a test set has on a particular gene in a particular cell type.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein. By the term insulin pen is meant an injection device suitable for applying discrete doses of insulin, where the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
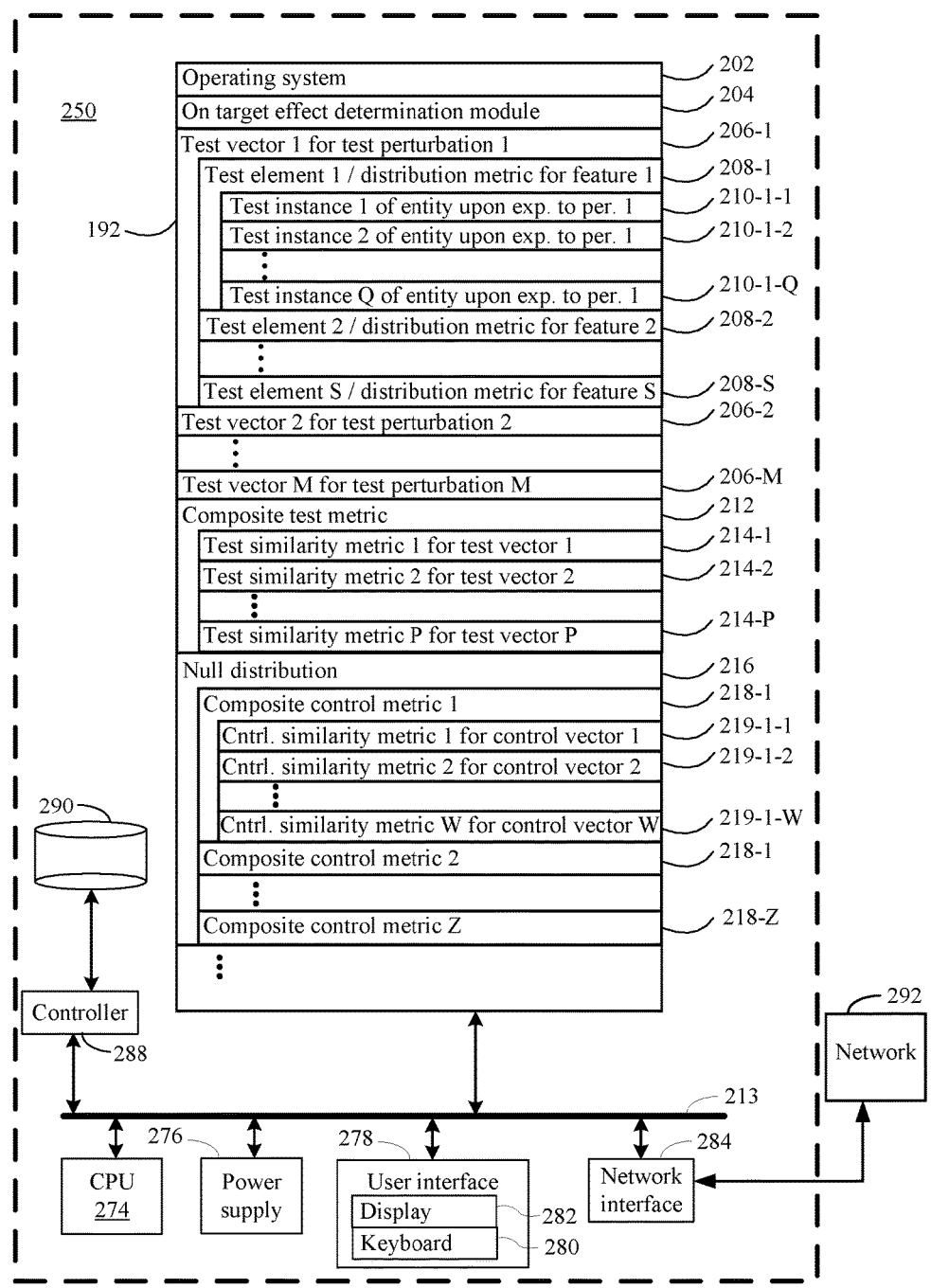
FIG. 2 illustrates a device for determining whether a set of test perturbations discriminate (e.g., differentiate) over a null distribution, formed using sets of control perturbations, for an on target effect against a first component of an entity, in accordance with an embodiment of the present disclosure.
Figure 3:
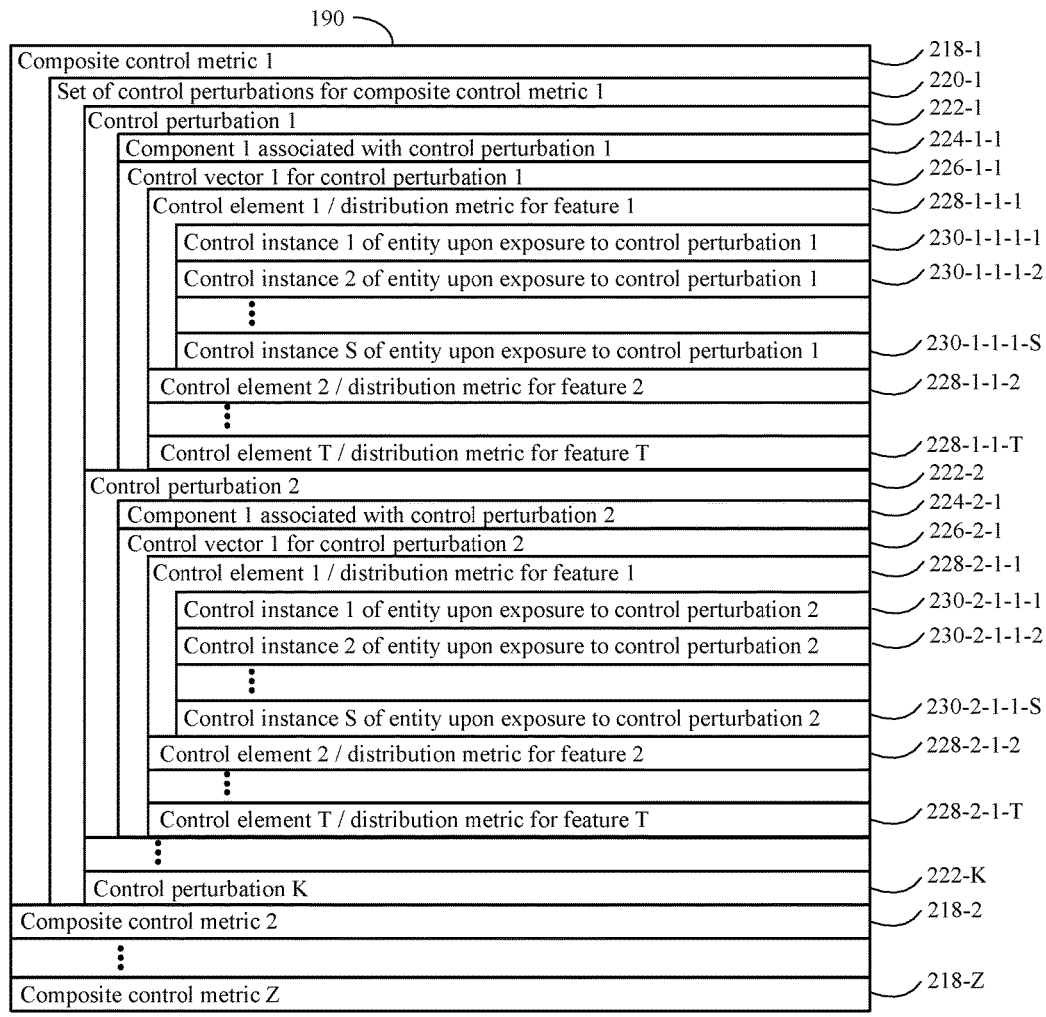
FIG. 3 illustrates data structures for determining whether a set of test perturbations discriminate (e.g., differentiate) over a null distribution, formed using sets of control perturbations, for an on target effect against a first component of an entity, in accordance with an embodiment of the present disclosure.

A detailed description of a system 250 for determining whether a set of test perturbations discriminate over a null distribution, formed using sets of control perturbations, in identifying an on target effect against a first component of an entity is described in conjunction with FIGS. 1 through 3. As such, FIGS. 1 through 3 collectively illustrate the topology of the system in accordance with the present disclosure. In the topology, there is a workflow for obtaining images 106 of multiwell plates 102. The images are used by an on target effect determination module 204 to extract numerous features from each well of the multiwell plate in the form of a data set 110. The dataset 110 is then processed as described in further detail below by system 250 of FIGS. 2 and 3 to determine whether a set of test perturbations has an on target effect against a first component of an entity.

Referring to FIG. 1, system 250 for determining whether a set of test perturbations has an on target effect against a first component of an entity. To do this, system 250 receives digital images 250 of multiwell plates 102, where each well of each multiwell plates contains a sample of an entity (e.g. cells) that have been exposed to one or more of a predetermined plurality of perturbations.

Referring to FIG. 2, in typical embodiments, system 250 comprises one or more computers. For purposes of illustration in FIG. 2, system 250 is represented as a single computer that includes all of the functionality for determining whether a set of test perturbations has an on target effect against a first component of an entity. However, the disclosure is not so limited. In some embodiments, the functionality for determining whether a set of test perturbations has an on target effect against a first component of an entity is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIGS. 2 and 3 with the foregoing in mind, an example system 250 for determining whether a set of test perturbations has an on target effect against a first component of an entity comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the system 250 but that can be electronically accessed by the system 250 over an Internet, intranet, or other form of network or electronic cable (illustrated as element 292 in FIG. 2) using network interface 284.

In some embodiments, the memory 192 of the system 250 for determining whether a set of test perturbations has an on target effect against a first component of an entity stores:

- an operating system 202 that includes procedures for handling various basic system services;
- an on target effect determination module 204;
- a respective test vector 206 for each test perturbation in a set of test perturbations of a first component of an entity, each respective test vector 206 comprising a plurality of test elements 208, each respective test element 208 associated with a distribution metric for a different feature corresponding to the respective test element, each test element 208 supported by a plurality of test instances 210 of the entity upon exposure to the test perturbation corresponding to the respective test vector 206;
- a composite test metric 212, where the composite test metric test metric 212 quantifies the on target effect of the set of test perturbations against the first component as a measure of central tendency across a plurality of test similarity metrics 214, where each test similarity metric 214 corresponds to a respective test vector 206 and therefore to a test perturbation in the set of test perturbations, and represents a similarity between (i) the respective test vector 206 and (ii) a measure of central tendency of the plurality of test vectors with the respective test vector removed from the plurality of test vectors; and
- a null distribution 216 comprising a plurality of composite control metrics 218, where each composite test metric test metric 212 is associated with a corresponding set of control perturbations 220, and where each control perturbation 222 in the corresponding set of control perturbations 220 is against a different component 224 in the plurality of components of the entity, and where there is a control vector 226 corresponding to each respective control perturbation 222 in the set of control perturbations 220, where each control vector comprises a plurality of control elements 228, each respective control element 228 comprising a distribution metric of a measurement of a different feature, in the plurality of features, across a respective plurality of control instances 230 of the entity upon exposure of the respective plurality of control instances of the entity to the respective control perturbation 222 and where each composite control metric 218 is computed as a distribution metric of a corresponding plurality of control similarity metrics 219, each control similarity metric 219 representing the similarity between a corresponding control vector 226 and a distribution metric of the respective plurality of control vectors of a control perturbation 222 with the respective control vector 226 removed from the respective plurality of control vectors.

In some embodiments, the on target effect determination module 204 is accessible within any browser (phone, tablet, laptop/desktop). In some embodiments the on target effect determination module 204 runs on native device frameworks, and is available for download onto the system 250 running an operating system 202 such as Android or iOS.

In some implementations, one or more of the above identified data elements or modules of the system 250 for determining whether a set of test perturbations has an on target effect against a first component of an entity are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, device 250 for determining whether a set of test perturbations has an on target effect against a first component of an entity is a smart phone (e.g., an iPHONE), laptop, tablet computer, desktop computer, or other form of electronic device. In some embodiments, the device 250 is not mobile. In some embodiments, the device 250 is mobile.

Now that details of a system 250 for determining whether a set of test perturbations has an on target effect against a first component of an entity have been disclosed, details regarding a flow chart of processes and features of the system, in accordance with an embodiment of the present disclosure, are disclosed with reference to FIGS. 4A through 4G. In some embodiments, such processes and features of the system are carried out by the on target effect determination module 204 illustrated in FIG. 2.

Block 402. With reference to block 402 of FIG. 4A, a computer system 250 for determining whether a set of test perturbations has an on target effect against a first component of an entity is provided. The set of test perturbations comprises a plurality of test perturbations of the first component and the entity comprises a plurality of components including the first component. The computer system comprises one or more processors 274, a memory 192/290, and one or more programs. The one or more programs are stored in the memory and are configured to be executed by the one or more processors. The one or more programs include instructions for performing a method.

In some embodiments, an entity is a cell culture, such as a cell line, primary cells, or a co-culture system. Examples of entities included, but are not limited to U2OS cells, A549 cells, MCF-7 cells, 3T3 cells, HTB-9 cells, HeLa cells, HepG2 cells, HEKTE cells, SH-SY5Y cells, HUVEC cells, HMVEC cells, primary human fibroblasts, and primary human hepatocyte/3T3-J2 fibroblast co-cultures. In some embodiments an entity is a culture of human cells.

In some embodiments, a component is a gene in the genome of an entity.

In some embodiments, a test perturbation is a small interfering RNA (siRNA) that specifically recognizes a component in an entity. Each siRNA is a double-stranded RNA molecule, 20-25 base pairs in length that interferes with the expression of a specific gene with a complementary nucleotide sequence by degrading mRNA after transcription preventing translation of the gene. An siRNA is an RNA duplex that can reduce gene expression through enzymatic cleavage of a target mRNA mediated by the RNA induced silencing complex (RISC). An siRNA has the ability to inhibit targeted genes with near specificity. See, Agrawal et al., 2003, "RNA interference: biology, mechanism, and applications," Microbiol Mol Biol Rev. 67: 657-85; and Reynolds et al., 2004, "Rational siRNA design for RNA interference," Nature Biotechnology 22, 326-330, each of which is hereby incorporated by reference. In some such embodiments, the perturbation is achieved by transfecting the siRNA into the entity, DNA-vector mediated production, or viral-mediated siRNA synthesis. See, for example, Paddison et al., 2002, "Short hairpin RNAs (shRNAs) induce sequence-specific silencing in mammalian cells," Genes Dev. 16:948-958; Sui et al., 2002, A DNA vector-based RNAi technology to suppress gene expression in mammalian cells," Proc Natl Acad Sci USA 99:5515-5520; Brummelkamp et al., 2002, "A system for stable expression of short interfering RNAs in mammalian cells," Science 296: 550-553; Paddison et al., 2004, "Short hairpin activated gene silencing in mammalian cells," Methods Mol Biol 265:85-100; Wong et al. 2003, "CIITAregulated plexin-A1 affects T-cell-dendritic cell interactions, Nat Immunol 2003, 4:891-898; Tomar et al., 2003, "Use of adeno-associated viral vector for delivery of small interfering RNA. Oncogene 22:5712-5715; Rubinson et al., 2003 "A lentivirus-based system to functionally silence genes in primary mammalian cells, stem cells and transgenic mice by RNA interference," Nat Genet 33:401-406; Moore et al., 2005, "Stable inhibition of hepatitis B virus proteins by small interfering RNA expressed from viral vectors," J Gene Med; and Tran et al., 2003, "Expressing functional siRNAs in mammalian cells using convergent transcription, BMC Biotechnol 3:21; each of which is hereby incorporated by reference.

In some embodiments, a test perturbation is material taken directly from cells or from fluids, tissues or organs of patients exhibiting a disease of interest (e.g. synovial fluid from rheumatoid arthritis patients). In some embodiments this material is referred to as a "conditioned medium." For instance, by way of example, in some embodiments the material is a synovial tissue explant (See, Beekhuizen et al., 2011, "Osteoarthritic synovial tissue inhibition of proteoglycan production in human osteoarthritic knee cartilage: establishment and characterization of a long-term cartilage-synovium coculture," Osteoarthritis 63, 1918, which is hereby incorporated by reference) that is either immediately used as a test perturbation or is cultured for a predetermined period of time prior to use as a perturbation. By way of another example, in some embodiments the material is mesenchymal stem cells (MSCs) that have been isolated and cultured from heparinized femoral-shaft marrow aspirate of human patients undergoing total hip arthroplasty, seeded in cell medium (e.g., Dulbecco's Modified Eagle Medium). See, Buul, 2012, "Mesenchymal stem cells secrete factors that inhibit inflammatory processes in short-term osteoarthritic synovium and cartilage explant culture," Osteoarthritis and Cartilage 20, 1186, which is hereby incorporated by reference. See also, Kay et al., 2017, "Mesenchymal Stem Cell-Conditioned Medium Reduces Disease Severity and Immune Responses in Inflammatory Arthritis," Nature 7, 18019, which is hereby incorporated by reference, for an example of the preparation of a condition medium in the form of murine MSCs isolated form BALB/C mice. By way of still another example, in some embodiments, the material is human synovial explants or cartilage explants obtained as surgical waste material from patients undergoing knee replacement surgery. In such embodiments, the perturbation is the material extracted directly from cells or from fluids, tissues or organs of patients exhibiting a disease of interest that is either used immediately after extraction, or after the material has been cultured for a period of time. In some embodiments, the material is cultured in the presence of factors that are intended to stimulate the material. For instance, in the case where the material is mesenchymal stem cells, in some embodiments, by way of example, the material is cultured in the presence of TNFα and IFNγ to stimulate the secretion of immunomodulatory factors by MSCs. See, Buul, 2012, Osteoarthritis and Cartilage 20, 1186, which is hereby incorporated by reference. For another example of the preparation of conditioned medium, see Martin, 1981, "Isolation of a pluripotent cell line from early mouse embryos cultured in medium conditioned by teratocarcinoma stem cells," PNAS 78, 7634, which is hereby incorporated by reference.

In some embodiments, a test perturbation is a short hairpin RNA (shRNA). See, Taxman et al., 2006, "Criteria for effective design, construction, and gene knockdown by shRNA vectors," BMC Biotechnology 6:7 (2006), which is hereby incorporated by reference. In some such embodiments, the perturbation is achieved by DNA-vector mediated production, or viral-mediated siRNA synthesis as generally discussed in the references cited above for siRNA.

In some embodiments, a test perturbation is single guide RNA (sgRNA) used in the context of palindromic repeat (CRISPR) technology. See, Sander and Young, 2014, "CRISPR-Cas systems for editing, regulating and targeting genomes," Nature Biotechnology 32, 347-355, hereby incorporated by reference, in which a catalytically-dead Cas9 (usually denoted as dCas9) protein lacking endonuclease activity to regulate genes in an RNA-guided manner. Targeting specificity is determined by complementary base-pairing of a single guide RNA (sgRNA) to the genomic loci. sgRNA is a chimeric noncoding RNA that can be subdivided into three regions: a 20 nt base-pairing sequence, a 42 nt dCas9-binding hairpin and a 40 nt terminator. In some embodiments, when designing a synthetic sgRNA for use as a perturbation, only the 20 nt base-pairing sequence is modified from the overall template. Additionally, in some embodiments, secondary variables are considered such as off target effects and maintenance of the dCas9-binding hairpin structure. In some embodiments, the Cas9 is rendered catalytically inactive by introducing point mutations in the two catalytic residues (D10A and H840A) of the gene encoding Cas9. See Jinek et al., 2012, "A Programmable Dual-RNA-Guided DNA Endonuclease in Adaptive Bacterial Immunity," Science 337, (6096), 816, which is hereby incorporated by reference. In doing so, dCas9 is unable to cleave dsDNA but retains the ability to target DNA. In some such embodiments, the perturbation is achieved by DNA-vector mediated production, or viral-mediated sgRNA synthesis as generally discussed in the references cited above for siRNA.

In some embodiments, a test perturbation is a cytokine or mixture of cytokines. See Heike and Nakahata, 2002, "Ex vivo expansion of hematopoietic stem cells by cytokines," Biochim Biophys Acta 1592, 313-321, which is hereby incorporated by reference, for suitable assays for exposing entities to perturbations in the form of cytokines (e.g., in vitro assays such as long-term culture-initiating cell (LTCIC) assay, cobblestone area-forming cell (CAFC) assay, high proliferative potential colony-forming cell (HPP-CFC) assay, and colony-forming unit-blast (CFU-Bl) assay, as well as in vivo assays using animal models). In some embodiments entities are exposed to perturbations in the form of cytokines (e.g., lymphokines, chemokines, interferons, tumor necrosis factors, etc.). In some embodiments entities are exposed to perturbations in the form of lymphokines (e.g., Interleukin 2, Interleukin 3, Interleukin 4, Interleukin 5, Interleukin 6, granulocyte-macrophage colony-stimulating factor, interferon gamma, etc.). In some embodiments entities are exposed to perturbations in the form of chemokines such as homeostatic chemokines (e.g., CCL14, CCL19, CCL20, CCL21, CCL25, CCL27, CXCL12, CXCL13, etc.) and/or inflammatory chemokines (e.g., CXCL-8, CCL2, CCL3, CCL4, CCL5, CCL11, CXCL10). In some embodiments entities are exposed to perturbations in the form of interferons (IFN) such as a type I IFN (e.g., IFN-α, IFN-β, IFN-c, IFN-κ and IFN-ω.), a type II IFN (e.g., IFN-γ), or a type III IFN. In some embodiments entities are exposed to perturbations in the form of tumor necrosis factors such as TNFα or TNF alpha.

In some embodiments, a test perturbation is a compound. In some such embodiments the activity of such a compound against an entity is assayed using a phosphoflow technique such as one disclosed in Krutzik et al., 2008, "High-content single-cell drug screening with phosphospecific flow cytometry," Nature Chemical Biology 4, 132-142, which is hereby incorporated by reference. In some embodiments the test perturbation is a compound having a molecular weight of less than 2000 Daltons. In some embodiments, the test perturbation is any organic compound having a molecular weight of less than 2000 Daltons, of less than 4000 Daltons, of less than 6000 Daltons, of less than 8000 Daltons, of less than 10000 Daltons, or less than 20000 Daltons.

In some embodiments, the test perturbation is a chemical compound that satisfies the Lipinski rule of five criteria. In some embodiments, the test perturbation is an organic compound that satisfies two or more rules, three or more rules, or all four rules of the Lipinski's Rule of Five: (i) not more than five hydrogen bond donors (e.g., OH and NH groups), (ii) not more than ten hydrogen bond acceptors (e.g. N and O), (iii) a molecular weight under 500 Daltons, and (iv) a Log P under 5. The "Rule of Five" is so called because three of the four criteria involve the number five. See, Lipinski, 1997, "Experimental and computational approaches to estimate solubility and permeability in drug discovery and development settings," Adv. Drug Del. Rev. 23, 3-26, which is hereby incorporated herein by reference in its entirety. In some embodiments, the test perturbation satisfies one or more criteria in addition to Lipinski's Rule of Five. For example, in some embodiments, the test perturbation is a compound with five or fewer aromatic rings, four or fewer aromatic rings, three or fewer aromatic rings, or two or fewer aromatic rings.

In some embodiments, a test perturbation is a protein perturbation such as a peptide aptamer. Peptide aptamers are combinatorial protein reagents that bind to target proteins with a high specificity and a strong affinity. By so doing, they can modulate the function of their cognate targets. In some embodiments, a peptide aptamer comprises one (or more) conformationally constrained short variable peptide domains, attached at both ends to a protein scaffold. Because peptide aptamers introduce perturbations that are similar to those caused by therapeutic molecules, their use identifies and/or validates therapeutic targets with a higher confidence level than is typically provided by methods that act upon protein expression levels. The combinatorial nature of peptide aptamers enables them to 'decorate' numerous polymorphic protein surfaces, whose biological relevance can be inferred through characterization of the peptide aptamers. Bioactive aptamers that bind druggable surfaces can be used in displacement screening assays to identify small-molecule hits to the surfaces. See, for example, Baines and Colas, 2006, "Peptide Aptamers as guides for small-molecule drug discovery," Drug Discovery Today 11, 334-341, which is hereby incorporated by reference. In some embodiments a test perturbation is a peptide aptamer, that is, an artificial protein selected or engineered to bind specific target molecules. In some such embodiments, a peptide aptamer comprises one or more peptide loops of variable sequence displayed by a protein scaffold. In some embodiments the peptide aptamer is isolated from a combinatorial library. In some embodiments such a combinatorial library isolate is further improved by directed mutation or rounds of variable region mutagenesis and selection. In some embodiments, libraries of peptide aptamers are used as "mutagens," in which a library that expresses different peptide aptamers is introduced into a population of entities, for selection of a desired phenotype, and an identification of those aptamers that cause the desired phenotype.

In some embodiments, a perturbation comprises a peptide aptamer derivatized with one or more functional moieties that can cause specific postranslational modification of their target proteins, or change the subcellular localization of the targets. See, for example, Colas et al., 2000, "Targeted modification and transportation of cellular proteins," Proc. Natl. Acad. Sci. USA. 97 (25): 13720-13725, which is hereby incorporated by reference. In some embodiments, the peptides that form the aptamer variable regions are synthesized as part of the same polypeptide chain as the scaffold and are constrained at their N and C termini by linkage to it. This double structural constraint decreases the diversity of the conformations that the variable regions can adopt. As a consequence, peptide aptamers can bind their targets tightly, with binding affinities comparable to those shown by antibodies (nanomolar range). Peptide aptamer scaffolds are typically small, ordered, soluble proteins. One such scaffold is *Escherichia coli* thioredoxin, the trxA gene product (TrxA). See, Reverdatto et al., 2015, "Peptide aptamers: development and applications," Curr. Top. Med. Chem. 15 (12): 1082-1101, which is hereby incorporated by reference. In these molecules, a single peptide of variable sequence is displayed instead of the Gly-Pro motif in the TrxA-Cys-Gly-Pro-Cys-active site loop. Improvements to TrxA include substitution of serines for the flanking cysteines, which prevents possible formation of a disulfide bond at the base of the loop, introduction of a D26A substitution to reduce oligomerization, and optimization of codons for expression in human cells. Reverdatto et al., further discloses other scaffolds that can be used, as does Škrlec et al., 2015, "Non-immunoglobulin scaffolds: a focus on their targets," Trends Biotechnol. 33 (7): 408-418, which is hereby incorporated by reference. In some embodiments, the peptide aptamers are selected yeast two-hybrid systems and/or combinatorial peptide libraries constructed by phage display and other surface display technologies such as mRNA display, ribosome display, bacterial display and yeast display (e.g., biopannings). In some embodiments, the perturbation is a peptide aptamer that uses a peptide in the MimoDB database. See Huang et al., 2011, "MimoDB 2.0: a mimotope database and beyond," Nucleic Acids Research. 40 (1): D271-D277, which is hereby incorporated by reference.

In some embodiments, a test perturbation is a peptide that selectively affects protein-protein interactions within an entity. In some such embodiments this protein-protein interaction affects an intracellular signaling event. See, for example, Souroujon and Mochly-Rosen, 1998, "Peptide modulators of protein-protein interactions in intracellular signaling," Nature Biotechnology 16, 919-924, which is hereby incorporated by reference.

In some embodiments, a test perturbation is a nucleic acid perturbation such as a nucleic acid aptamer. Nucleic acid aptamers are short synthetic single-stranded oligonucleotides that specifically bind to various molecular targets such as small molecules, proteins, nucleic acids, and even cells and tissues. See, Ni et al., 2011, "Nucleic acid aptamers: clinical applications and promising new horizons," Curr Med Chem 18(27), 4206, which is hereby incorporated by reference. In some instance nucleic acid aptamers are selected from a biopanning method such as SELEX (Systematic Evolution of Ligands by Exponential enrichment).

See, Ellington and Szostak, 1990, "In vitro selection of RNA molecules that bind specific ligands," Nature 346(6287), 818; and Tuerk and Gold, 1990, "Systematic evolution of ligands by exponential enrichment: RNA ligands to bacteriophage T4 DNA polymerase," Science 249(4968), 505, each of which is hereby incorporated by reference. The SELEX screening method begins with a random sequence library of ssDNA or ssRNA that spans 20-100 nucleotides (nt) in length. The randomization of nucleic acid sequences provides a diversity of $4_n$, with n corresponding to the number of randomized bases. Diversities on the order of $\sim 10^{16}$ aptamers can typically generated and screened in the SELEX methods. Each random sequence region is flanked by constant sequences that is used for capture or priming. To overcome exonuclease degradation, aptamers can be chemically synthesized and capped with modified or inverted nucleotides to prevent terminal degradation. Modified oligonucleotides can also be incorporated within the aptamer, either during or after selection, for enhanced endonuclease stability. Some modified nucleotide triphosphates, particularly 2'-O-modified pyrimidines, can be efficiently incorporated into nucleic acid aptamer transcripts by T7 RNA polymerases. Common chemical modifications included during selection are 2'-amino pyrimidines and 2'-fluoro pyrimidines. See, Ni et al., 2011, "Nucleic acid aptamers: clinical applications and promising new horizons," Curr Med Chem 18(27), 4206, which is hereby incorporated by reference.

In some embodiments, a test perturbation is an antibody or other form of biologic. In some embodiments, a library of test perturbations is used, where each member of the library is a different antibody. In some such embodiments, the library of antibodies comprises 100 antibodies, 1000 antibodies, or ten thousand antibodies. In some such embodiments, libraries of antibodies are generated using phage display techniques such as those disclosed in Wu et al., 2010, "Therapeutic antibody targeting of individual Notch receptors," Nature 464, 1052-1057, which is hereby incorporated by reference. In some embodiments, a library of test perturbations is used, where each member of the library is a different biologic. In some such embodiments, the library of biologics comprises 100 biologics, 1000 biologics, or ten thousand biologics. In some such embodiments, entities are exposed to perturbations in the form of antibodies. For instance, in some such embodiments, such antibodies selectively bind to a transmembrane protein expressed by the entities, causing a cascading signal that selectively regulates a transcriptional program within the entity. For instance, as disclosed in Wu et al., id., receptors within the Notch family are widely expressed transmembrane proteins that function as key conduits through which mammalian cells communicate to regulate cell fate and growth. Ligand binding triggers a conformational change in the receptor negative regulatory region (NRR) that enables ADAM (a disintegrin and metalloproteinases) protease cleavage at a juxtamembrane site that otherwise lies buried within the quiescent NRR. Subsequent intramembrane proteolysis catalyzed by the c-secretase complex liberates the intracellular domain (ICD) to initiate the downstream Notch transcriptional program. Thus, in some embodiments, the test perturbation is an antibody that is exposed to the entity thereby causing a selective change in the transcription of one or more components within the entity.

In some embodiments, a test perturbation is a zinc finger transcription factor. In some such embodiments, the zinc finger protein transcription factor is encoded into vector that is transformed into the entity, thereby causing the control of expression of one or more targeted components within the entity. In some such embodiments, a sequence that is common to multiple (e.g., functionally related) components in the entity is used by a perturbation in the form of a zinc finger protein in order to control the transcription of all these component with a single perturbation in the form of a zinc finger transcription factor. In some embodiments, the perturbation in the form of a zinc finger transcription factor targets a family of related components in an entity by targeting and modulating the expression of the endogenous transcription factors that control them. See, for example, Doyon, 2008, "Heritable targeted gene disruption in zebrafish using designed zinc-finger nucleases," Nature Biotechnology 26, 702-708, which is hereby incorporated by reference.

In some embodiments, each test perturbation builds confidence around the specificity of a biological signal related to a specific disease or other form of biological signal under study, for example, a particular phenotype exhibited by the test entity) by uniquely inhibiting a component in a biological pathway that is proximal (related) to the disease (or other form of biological signal under study) while each control perturbation has effects of similar magnitude on components of entity that are not proximal to the components of the biological signal under study. As such, in some embodiments the set of test perturbations provide a biological effect by targeting genetic components of the entity associated with the biological signal (e.g., disease) under study whereas the control perturbations target genetic components of the entity that are not proximal to the biological signal under study.

In some embodiments, each test perturbation and each control perturbation is an siRNA, an sgRNA, or an shRNA.

Block 404.

Figure 4A:
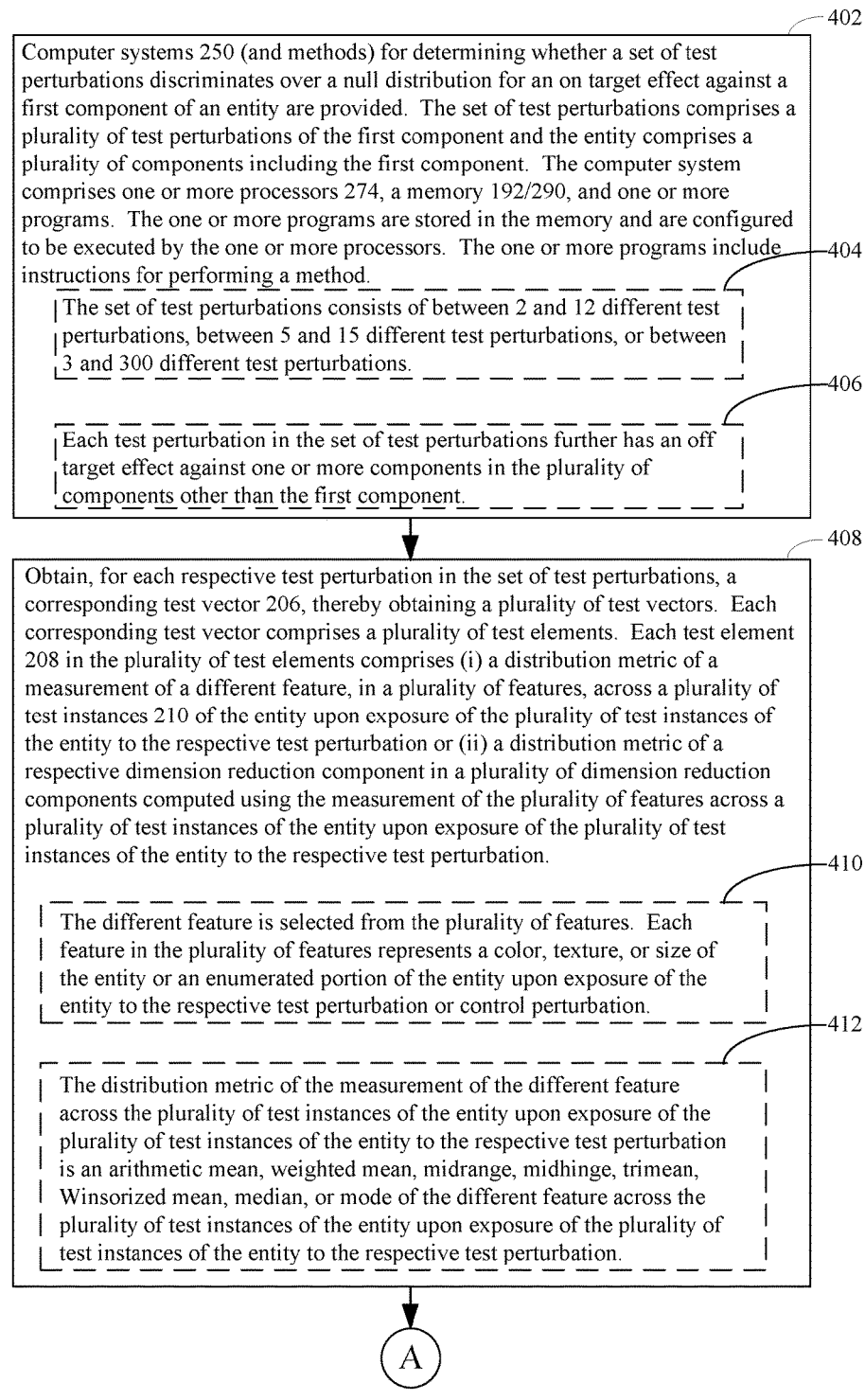

With reference to block 404 of FIG. 4A, in some embodiments the set of test perturbations consists of between 2 and 12 different test perturbations, between 5 and 15 different test perturbations, between 6 and 50 different test perturbations, or between 3 and 300 different test perturbations.

Block 406.

With reference to block 406 of FIG. 4A, in some embodiments the test perturbation in the set of test perturbations further has an off target effect against one or more components in the plurality of components other than the first component.

Block 408.

With reference to block 408 of FIG. 4A, there is obtained, for each respective test perturbation in the set of test perturbations, a corresponding test vector 206, thereby obtaining a plurality of test vectors. Each corresponding test vector 206 comprises a plurality of test elements.

In some embodiments, each test element 208 in the plurality of test elements comprises a distribution metric of a measurement of a different feature, in a plurality of features, across a plurality of test instances 210 of the entity upon exposure of the plurality of test instances of the entity to the respective test perturbation.

In some embodiments such data is acquired using an automated cellular imaging system (e.g., ImageXpress Micro, Molecular Devices), where entities have been arranged in multiwell plates (e.g., 384-well plates) after they have been stained with a panel of dyes that emit at different discrete wavelengths (e.g., Hoechst 33342, Alexa Fluor 594 phalloidin, etc.) and exposed to a perturbation. In some embodiments the entities are imaged with an exposure that is a determined by the marker dye used (e.g., 15 ms for Hoechst, 1000 ms for phalloidin), at 20× magnification with 2× binning. For each well, in some embodiments the optimal focus is found using laser auto-focusing on a particular dye channel (e.g., the Hoechst channel). In some embodiments the automated microscope is then programmed to collect a z-stack of 32 images (z=0 at the optimal focal plane, 16 images above the focal plane, 16 below) with 2 µm between slices. In some embodiments each well contains several thousand entities in them, and thus each digital representation of a well captured by a cameral represents several thousand entities in each of several different wells. In some embodiments, segmentation software is used to identify individual entities in the digital images and moreover various components (e.g., cellular components) within individual entities. Once the cellular components are segmented and identified, mathematical transformations are performed on these components on order to obtain the measurements of features.

As such, to illustrate, in the case where the set of test perturbations is five test perturbations, there will be five test vectors 206, that is, a test vector 206 for each test perturbation in the set of five test perturbations. Moreover, each test vector 206 will comprise a plurality of test elements, (e.g. five or more test elements 208, ten or more test elements 208, twenty or more test elements 208, 100 or more test elements 208, or one thousand or more test elements).

In some embodiments, each test element 208 in a test vector represents a different feature in a plurality of features that is measured from test instances of the test entity 210 upon exposure to the test perturbation. For instance, consider the case of a first test vector 206 corresponding to a first test perturbation, where the first test vector comprises 20 elements. Each test element represents a different feature that is measured from test instances of the entity upon exposure to the first test perturbation. The first test element 208 in the first test vector 206 represents the measurement of the first test feature in each of a plurality of test instances 210 of the entity upon exposure to the first perturbation. More specifically, each test element 208 represents a distribution metric of a corresponding test feature that is measured from each of the test instances 210 of the test entity upon exposure to a test perturbation corresponding to the test vector 206 that contains the test element 208.

The measurement of the plurality of features across a plurality of test instances of the entity upon exposure of the plurality of test instances of the entity to a respective perturbation in the plurality of perturbations results in an N-dimensional space, where each integer in the N-dimensional space is a different feature in the plurality of features.

In some alternative embodiments, each test element 208 in the plurality of test elements comprises a distribution metric of a respective dimension reduction component in a plurality of dimension reduction components computed using the measurement of the plurality of features across a plurality of test instances of the entity upon exposure of the plurality of test instances of the entity to the respective test perturbation. Such embodiments are advantageous because they eliminate or reduce redundancy between highly correlated features like size, area of the nucleus and perimeter of the nucleus of an entity.

For instance, referring to FIG. 5, in some embodiments, a dimension reduction technique (e.g., principal component analysis, subset selection, or a shrinkage method) is applied to the observations $p_{m,q,n}$ acquired across each entity in a plurality of entities, where each entity in each plurality of entities has been exposed to a control perturbation in a plurality of control perturbations. In some such embodiments this plurality of control perturbations is the same plurality of control perturbations that is used in blocks 448 through 474 described below. That is, the control perturbations that are used in blocks 448 through 474 described below are used to learn a reduced dimension space in the form of a plurality of dimension reduction components. In such embodiments, the control vectors of FIG. 3 are used to identify the dimension reduction components.

In some alternative embodiments, the plurality of control perturbations used to learn the reduced dimensional space is a different set of control perturbations than those used in block 448 through 474. In such embodiments, a plurality of features is measured multiple times for each perturbation in this set of control perturbations in a manner analogous to that disclosed in FIG. 3 and describe below with reference to blocks 448 through 474 and then this data is used to determine the plurality of dimension reduction components.

In some embodiments the plurality of perturbations used for dimension reduction comprise 200 or more control perturbations, 300 or more control perturbations, 400 or more control perturbations or 500 or more control perturbations.

In some embodiments each perturbation in the set of control perturbations that is used for dimension reduction targets and inhibits a particular component in the plurality of components of an entity. In some embodiments, the plurality of control perturbations comprise siRNA where each such siRNA specifically binds to and therefore inhibits the mRNA of a particular gene in a cell.

As such, referring to FIG. 5, there are a plurality of observations for each feature N in the plurality of features observed for the plurality of control perturbations that form the basis of the dimension reduction, and the N features can be considered an N-dimensional feature space. Thus, referring to FIG. 5, each horizontal line constitutes a vector of observations with N elements, and the collective set of vectors of dimension N can be subjected to a feature reduction technique to derive a set of dimension reduction components based on observed variation of individual elements in the N-dimensional vectors across the dataset. As such, the dimension reduction technique is used to identity a plurality of dimension reduction components where the plurality of dimension reduction components collectively represents the variance observed in the features from the N-dimensional feature space across all the measured instances of the control entities.

The plurality of dimension reduction components is then used to represent the set of first features 208-1 through 208-N from the N-dimensional feature space. However, it is not necessarily the case that the observations of a given feature 208 in the plurality of features 208 contributes to a particular dimension reduction component. For instance, the dimension reduction analysis of the control data may determine that some of the features do not contribute to explaining observed variation and thus the dimension reduction analysis does not incorporate these features into any of the dimension reduction components. Thus, in such embodiments, the plurality of features (N features) across the plurality of control instances of the entity upon exposure of the plurality of control instances of the entity of FIG. 5 are first subjected to a dimension reduction thereby computing the plurality of dimension reduction components (T dimension reduction components) where T is a positive integer less than N. Thus, in a case where the set of features is one thousand features, there will be less than five hundred dimension reduction components.

Referring to FIG. 6, once the dimension reduction components have been identified using a control set of perturbations, they can be applied to the observed features from the test entities exposed to test perturbations. In such instances, each respective test vector will represent a perturbation in the plurality of test perturbations and each respective element of each respective test vector will include a value for a corresponding dimension reduction component, from the plurality of dimension reduction components, based on the values of the test features represented by the dimension reduction component across the entities that have been exposed to the test perturbation that corresponds to the respective test vector.

Block 410.

Referring to block 410 of FIG. 4A, each of the features used to form the basis of elements of vectors 206 or used as a basis for a dimension reduction component is selected from a plurality of features. Each feature in the plurality of features represents a color, texture, or size of the entity or an enumerated portion of the entity upon exposure of the entity to the respective test perturbation or control perturbation. Example features include, but are not limited to entity area, entity perimeter, entity aspect ratio, actin content, actin texture, entity solidity, entity extent, entity nuclear area, entity nuclear perimeter, entity nuclear aspect ratio, to name a few such features. In some embodiment, example features include but are not limited to any of the features found in Table S2 of the reference Gustafsdottir and Ljosa, et al., 2013, PLOS Tenth Anniversary, https://doi.org/10.1371/journal.pone.0080999, accessed Nov. 19, 2017, which is hereby incorporated by reference. In some embodiments, such features are measured and acquired using the software program Cellprofiler. See Carpenter et al., 2006, "CellProfiler: image analysis software for identifying and quantifying cell phenotypes," Genome Biol. 7, R100 PMID: 17076895; Kamentsky et al., 2011, "Improved structure, function, and compatibility for CellProfiler: modular high-throughput image analysis software," Bioinformatics 201 l/doi. PMID: 21349861 PMCID: PMC3072555; and Jones et al., 2008, CellProfiler Analyst: data exploration and analysis software for complex image-based screens, BMC Bioinformatics 9(1):482/doi: 10.1186/1471-2105-9-482. PMID: 19014601 PMCID: PMC261443, each of which is hereby incorporated by reference.

In some embodiments one or more of the features that are observed for an entity, or a plurality of entities, are obtained using a whole transcriptome shotgun sequencing (RNA-Seq) experiment that quantifies gene expression from entities (e.g., single entity) in counts of transcript reads mapped to the components of the entity. As such, in some embodiments, RNA-Seq experiments aim at reconstructing all full-length mRNA transcripts of components concurrently from millions of short reads. RNA-Seq facilitates the ability to look at alternative gene spliced transcripts, post-transcriptional modifications, gene fusion, mutations/SNPs and changes in gene expression over time, or differences in gene expression in different groups or treatments. See, for example, Maher et al., 2009, "Transcriptome sequencing to detect gene fusions in cancer," Nature. 458 (7234): 97-101, which is hereby incorporated by reference. In addition to mRNA transcripts, RNA-Seq can evaluate and quantify individual members of different populations of RNA including total RNA, mRNA, miRNA, lncRNA, snoRNA, or tRNA within entities. As such, in some embodiments, one or more of the features that is observed for an entity is individual amounts of specific RNA species as determined using RNA-Seq techniques. In some embodiments, RNA-Seq experiments produce counts of component (e.g., digital counts of mRNA reads) that are affected by both biological and technical variation. In some embodiments RNA-Seq assembly is performed using the techniques disclosed in Li et al., 2008, "IsoLasso: A LASSO Regression Approach to RNA-Seq Based Transcriptome Assembly," Cell 133, 523-536 which is hereby incorporated by reference.

In some embodiments one or more of the features that are observed for an entity, or a plurality of entities, are obtained using transcriptional profiling methods such an L1000 panel that measures a set of informative transcripts. In such an approach, ligation-mediated amplification (LMA) followed by capture of the amplification products on fluorescently addressed microspheres beads is extended to a 1,000-plex reaction. For instance, cells growing in 384-well plates are lysed and mRNA transcripts are captured on oligo-dT-coated plates. cDNAs are synthesized from captured transcripts and subjected to LMA using locus-specific oligonucleotides harboring a unique 24-mer barcode sequence and a 5' biotin label. The biotinylated LMA products are detected by hybridization to polystyrene microspheres (beads) of distinct fluorescent color, each coupled to an oligonucleotide complementary to a barcode, and then stained with streptavidin-phycoerythrin. In this way, each bead can be analyzed both for its color (denoting landmark identity) and fluorescence intensity of the phycoerythrin signal (denoting landmark abundance). See Subramanian et al., "A Next Generation Connectivity Map: L1000 Platform and the First 1,000,000 Profiles," Cell 171(6), 1437, which is hereby incorporated by reference. In some embodiments, between 500 and 1500 different informative transcripts are measured using this assay.

In some embodiments one or more of the features that are observed for an entity, or a plurality of entities, are obtained using microarrays. A microarray (also termed a DNA chip or biochip) is a collection of microscopic nucleic acid spots attached to a solid surface that can be used to measure the expression levels of large numbers of genes simultaneously. Each nucleic acid spot contains picomoles of a specific nucleic acid sequence, known as probes (or reporters or oligos). These can be a short section of a gene or other nucleic acid element that are used to hybridize a cDNA or cRNA (also called anti-sense RNA) sample (called target) under high-stringency conditions. For instance, by way of a non-limiting example, in some embodiments, the microarrays such as the Affymetrix GeneChip microarray, a high density oligonucleotide gene expression array, is used. Each gene on an Affymetrix microarray GeneChip is typically represented by a probe set consisting of 11 different pairs of 25-bp oligos covering features of the transcribed region of that gene. Each pair consists of a perfect match (PM) and a mismatch (MM) oligonucleotide. The PM probe exactly matches the sequence of a particular standard genotype, often one parent of a cross, while the MM differs in a single substitution in the central, $13^{th}$ base. The MM probe is designed to distinguish noise caused by non-specific hybridization from the specific hybridization signal. See, Jiang, 2008, "Methods for evaluating gene expression from Affymetrix microarray datasets," BMC Bioinformatics 9, 284, which is hereby incorporated by reference.

In some embodiments one or more of the features that is observed for an entity, or a plurality of entities, are obtained from ChIP-Seq data. See, for example, Quigley and Kintner, 2017, "Rfx2 Stabilizes Foxj1 Binding at Chromatin Loops to Enable Multiciliated Cell Gene Expression," PLoS Genet 13, e1006538, which is hereby incorporated by reference. In some embodiments, ChIP-seq is used to determine how transcription factors and other chromatin-associated proteins influence phenotype-affecting mechanisms in entities (e.g., cells). Specific DNA sites in direct physical interaction with transcription factors and other proteins can be isolated by chromatin immunoprecipitation. ChIP produces a library of target DNA sites bound to a protein of interest (component) in vivo. Parallel sequence analyses are then used in conjunction with whole-genome sequence databases to analyze the interaction pattern of any protein with DNA (Johnson et al., 2007, "Genome-wide mapping of in vivo protein—DNA interactions," Science. 316: 1497-1502, which is hereby incorporated by reference) or the pattern of any epigenetic chromatin modifications. This can be applied to the set of ChIP-able proteins and modifications, such as transcription factors, polymerases and transcriptional machinery, structural proteins, protein modifications, and DNA modifications. ChIP selectively enriches for DNA sequences bound by a particular protein (component) in living cells (entities). The ChIP process enriches specific crosslinked DNA-protein complexes using an antibody against the protein (component) of interest. Oligonucleotide adaptors are then added to the small stretches of DNA that were bound to the protein of interest to enable massively parallel sequencing. After size selection, all the resulting ChIP-DNA fragments are sequenced concurrently using a genome sequencer. A single sequencing run can scan for genome-wide associations with high resolution, meaning that features can be located precisely on the chromosomes. Various sequencing methods can be used. In some embodiments the sequences are analyzed using cluster amplification of adapter-ligated ChIP DNA fragments on a solid flow cell substrate to create clusters of clonal copies. The resulting high density array of template clusters on the flow cell surface is sequenced by a Genome analyzing program. Each template cluster undergoes sequencing-by-synthesis in parallel using fluorescently labelled reversible terminator nucleotides. Templates are sequenced base-by-base during each read. Then, the data collection and analysis software aligns sample sequences to a known genomic sequence to identify the ChIP-DNA fragments.

In some embodiments one or more of the features that is observed for an entity, or for a plurality of entities, are obtained from ATAC-seq (Assay for Transposase-Accessible Chromatin using sequencing), which is a technique used in molecular biology to study chromatin accessibility. See Buenrostro et al., 2013, "Transposition of native chromatin for fast and sensitive epigenomic profiling of open chromatin, DNA-binding proteins and nucleosome position," Nature Methods 10, 1213-1218, which is hereby incorporated by reference. In some embodiments, ATAC-seq make use of the action of the transposase Tn5 on the genomic DNA of an entity. See, for example, Buenrostro et al., 2015, "ATAC-seq: A Method for Assaying Chromatin Accessibility Genome-Wide," Current Protocols in Molecular Biology: 21.29.1-21.29.9, which is hereby incorporated by reference. Transposases are enzymes catalyzing the movement of transposons to other parts in the genome. While naturally occurring transposases have a low level of activity, ATAC-seq employs a mutated hyperactive transposase. The high activity allows for highly efficient cutting of exposed DNA and simultaneous ligation of specific sequences, called adapters. Adapter-ligated DNA fragments are then isolated, amplified by PCR and used for next generation sequencing. See Buenrostro et al., 2013, "Transposition of native chromatin for fast and sensitive epigenomic profiling of open chromatin, DNA-binding proteins and nucleosome position," Nature Methods 10, 1213-1218, which is hereby incorporated by reference.

While not intending to be limited to any particular theory, transposons are believed to incorporate preferentially into genomic regions free of nucleosomes (nucleosome-free regions) or stretches of exposed DNA in general. Thus enrichment of sequences from certain loci in the genome indicates absence of DNA-binding proteins or nucleosome in the region. An ATAC-seq experiment will typically produce millions of next generation sequencing reads that can be successfully mapped on the reference genome. After elimination of duplicates, each sequencing read points to a position on the genome where one transposition (or cutting) event took place during the experiment. One can then assign a cut count for each genomic position and create a signal with base-pair resolution. This signal is used as a features in some embodiments of the present disclosure. Regions of the genome where DNA was accessible during the experiment will contain significantly more sequencing reads (since that is where the transposase preferentially acts), and form peaks in the ATAC-seq signal that are detectable with peak calling tools. In some embodiments, such peaks, and their locations in the genome are used as features. In some embodiments, these regions are further categorized into the various regulatory element types (e.g., promoters, enhancers, insulators, etc.) by integrating further genomic and epigenomic data such as information about histone modifications or evidence for active transcription. Inside the regions where the ATAC-seq signal is enriched, one can also observe sub-regions with depleted signal. These subregions, typically only a few base pairs long, are considered to be "footprints" of DNA-binding proteins. In some embodiments, such footprints, or their absence or presence thereof are used as features.

In some embodiments one or more of the features that are observed for an entity, or a plurality of entities, is obtained from a high-throughput reduced representation expression profiling method, termed L1000, that is disclosed in Subramanian et al., 2017, "A Next Generation Connectivity Map: L1000 Platform and the First 1,000,000 Profiles," Cell 171, 1437-1452, which is hereby incorporated by reference. L1000 measures the mRNA transcript abundance of 978 "landmark" genes from human cells. (The "L" in L1000 refers to the Landmark genes measured in the assay.) Measurements are made using the 500 colors of Luminex beads such that two transcripts are identified by a single bead color. The expression of 80 control transcripts, chosen for their invariant expression across cell states, is also measured. L1000 measures a highly representative subset of the transcriptome, capturing a large fraction of information at a small fraction of cost compared to other expression profiling technologies. In some embodiments, measurements of these 978 "landmark genes" are applied to an inference algorithm to infer the expression of 11,350 additional genes in the transcriptome. In some embodiments, the measured expression of the 979 landmark genes serve as features in the present disclosure. In some embodiments, the inferred expression of the 11,350 additional genes are used as features in the present disclosure.

In some embodiments flow cytometry methods using Luminex beads are used to obtain values for one or more of the features that are observed for an entity or a plurality of entities. See for example, Süsal et al., 2013, Transfus Med Hemother 40, 190-195, which is hereby incorporated by reference. For instance, the Luminex-supported single antigen beat (L-SAB) test allows for the characterization of human leukocyte antigen (HLA) antibody specificities. In such a flow cytometric method, microbeads coated with recombinant single antigen HLA molecules are employed in order to differentiate antibody reactivity in two reaction tubes against 100 different HLA class I and 100 different HLA class II alleles. An approximation of the strength of antibody reactivity is derived from the mean fluorescence intensity (MFI) and in some embodiments this serves as features in the present disclosure. In addition to antibody reactivity against HLA-A, -B, -C, -DR and -DQB antigens, L-SAB is capable of detecting antibodies against HLA-DQA, -DPA, and -DPB antigens. In some embodiments, other Luminex kits are used for detection of non-HLA antibodies in order to derive values for one or more features for entities in accordance with the present disclosure. For instance, in some embodiments, major histocompatibility complex class I-related chain A (MICA) and human neutrophil antibodies, and kits that utilize, instead of recombinant HLA molecules, affinity purified pooled human HLA molecules obtained from multiple cell lines (screening test to detect presence of HLA antibodies without further specification) or phenotype panels in which each bead population bears either HLA class I or HLA class II proteins of a cell lines derived from a single individual (panel reactivity, PRA-test) are used to determine value for features for entities in accordance with an embodiment of the present disclosure.

In some embodiments, flow cytometry methods, such fluorescent cell barcoding, is used to obtain values for one or more of the features that are observed for an entity. Fluorescent cell barcoding (FCB) enables high throughput, e.g. high content flow cytometry by multiplexing samples of entities prior to staining and acquisition on the cytometer. Individual cell samples (entities) are barcoded, or labeled, with unique signatures of fluorescent dyes so that they can be mixed together, stained, and analyzed as a single sample. By mixing samples prior to staining, antibody consumption is typically reduced 10 to 100-fold. In addition, data robustness is increased through the combination of control and treated samples, which minimizes pipetting error, staining variation, and the need for normalization. Finally, speed of acquisition is enhanced, enabling large profiling experiments to be run with standard cytometer hardware See, for example, Krutzik, 2011, "Fluorescent Cell Barcoding for Multiplex Flow Cytometry," Curr Protoc Cytom Chapter 6: Unit 6.31, which is hereby incorporated by reference.

In some embodiments, metabolomics is used to obtain values for one or more of the features that are observed for an entity or a plurality of entities. Metabolomics is a systematic evaluation of small molecules in order to obtain biochemical insight into disease pathways. In some embodiments, such metabolomics comprises evaluation of plasma metabolomics in diabetes (Newgard et al., 2009, "A branched-chain amino acid-related metabolic signature that differentiates obese and lean humans and contributes to insulin resistance," Cell Metab 9: 311-326, 2009) and ESRD (Wang, 2011, "RE: Metabolite profiles and the risk of developing diabetes," Nat Med 17: 448-453). In some embodiments urine metabolomics is used to obtain values for one or more of the features. Urine metabolomics offers a wider range of measurable metabolites because the kidney is responsible for concentrating a variety of metabolites and excreting them in the urine. In addition, urine metabolomics may offer direct insights into biochemical pathways linked to kidney dysfunction. See, for example, Sharma, 2013, "Metabolomics Reveals Signature of Mitochondrial Dysfunction in Diabetic Kidney Disease," J Am Soc Nephrol 24, 1901-12, which is hereby incorporated by reference.

In some embodiments, mass spectrometry is used to obtain values for one or more of the features that are observed for an entity or a plurality of entities. For instance, in some embodiments, protein mass spectrometry is used to obtain values for one or more of the features that are observed for an entity or a plurality of entities. In particular, in some embodiments, biochemical fractionation of native macromolecular assemblies within entities followed by tandem mass spectrometry is used to obtain values for one or more of the features that are observed for an entity or a plurality of entities. See, for example, Wan et al., 2015, "Panorama of ancient metazoan macromolecular complexes," Nature 525, 339-344, which is hereby incorporated by reference. Tandem mass spectrometry, also known as MS/MS or MS2, involves multiple steps of mass spectrometry selection, with some form of fragmentation occurring in between the stages. In a tandem mass spectrometer, ions are formed in the ion source and separated by mass-to-charge ratio in the first stage of mass spectrometry (MS1). Ions of a particular mass-to-charge ratio (precursor ions) are selected and fragment ions (product ions) are created by collision-induced dissociation, ion-molecule reaction, photodissociation, or other process. The resulting ions are then separated and detected in a second stage of mass spectrometry (MS2). In some embodiments the detection and/or presence of such ions serve as the one or more of the features that are observed for an entity or a plurality of entities.

In some embodiments, the features that are observed for an entity or a plurality of entities are post-translational modifications that modulate activity of proteins within such entities. In some such embodiments, mass spectrometric peptide sequencing and analysis technologies are used to detect and identify such post-translational modifications. In some embodiments, isotope labeling strategies in combination with mass spectrometry are used to study the dynamics of modifications and this serves as the features that are observed for an entity or a plurality of entities. See for example, Mann and Jensen, 2003 "Proteomic analysis of post-translational modifications," Nature Biotechnology 21, 255-261, which is hereby incorporated by reference. In some embodiments, mass spectrometry is user to determine splice variants in entities, for instance, splice variants of components within entities, and such splice variants and the detection of such splice variants serve as measured features for one or more entities. See for example, Nilsen and Graveley, 2010, "Expansion of the eukaryotic proteome by alternative splicing, 2010, Nature 463, 457-463, which is hereby incorporated by reference.

In some embodiments, imaging cytometry is used to obtain values for one or more of the features that are observed for an entity or a plurality of entities. Imaging flow cytometry combines the statistical power and fluorescence sensitivity of standard flow cytometry with the spatial resolution and quantitative morphology of digital microscopy. See, for example, Basiji et al., 2007, "Cellular Image Analysis and Imaging by Flow Cytometry," Clinics in Laboratory Medicine 27, 653-670, which is hereby incorporated by reference.

In some embodiments, electrophysiology is used to obtain values for one or more of the features that are observed for an entity or a plurality of entities. See, for example, Dunlop et al., 2008, "High-throughput electrophysiology: an emerging paradigm for ion-channel screening and physiology," Nature Reviews Drug Discovery 7, 358-368, which is hereby incorporated by reference.

In some embodiments, proteomic imaging/3D imaging is used to obtain values for one or more of the features that are observed for an entity or a plurality of entities. See for example, United States Patent Publication No. 20170276686 A1, entitled "Single Molecule Peptide Sequencing," which is hereby incorporated by reference. Such methods can be used to large-scale sequencing of single peptides in a mixture from an entity, or a plurality of entities at the single molecule level.

In some embodiments, a feature represents a measurement of entities after the such entities have been exposed to a perturbation (e.g., an siRNA) as well as a panel of fluorescent stains that emit at different wavelengths such as Concanavalin A/Alexa Fluor 488 conjugate (Invitrogen, cat. no. C11252), Hoechst 33342 (Invitrogen, cat. no. H3570), SYTO 14 green fluorescent nucleic acid stain (Invitrogen, cat. no. S7576), Phalloidin/Alexa Fluor 568 conjugate (Invitrogen, cat. no. A12380), and MitoTracker Deep Red (Invitrogen, cat. no. M22426). In some embodiments, measured features include staining intensities, textural patterns, size, and shape of the labeled cellular structures, as well as correlations between stains across channels, and adjacency relationships between cells and among intracellular structures. In some embodiments, two, three, four, five, six, seven, eight, nine, ten, or more than 10 fluorescent stains, imaged in two, three, four, five, six, seven, or eight channels, is used to measure features in entities include different cellular components or compartments within such entities. In some embodiments, features are measured from single entities. In some embodiments, features are measured from a compartment or a component (e.g., nucleus, endoplasmic reticulum, nucleoli, cytoplasmic RNA, F-actin cytoskeleton, Golgi, plasma membrane, mitochondira) of a single entity. In some embodiments, each channel comprises (i) an excitation wavelength range and (ii) a filter wavelength range in order to capture the emission of a particular dye from among the set of dyes the entity has been exposed to prior to measurement. An example of the dye that is being invoked and the type of entity component that is measured for features for five suitable channels is provided in Table 1 below, which is adapted from Table 1 of Bray et al., 2016, "Cell Painting, a high-content image-based assay for morphological profiling using multiplexed fluorescent dyes," Nature Protocols, 11, p. 1757-1774, which is hereby incorporated by reference.

TABLE 1 example channels used for measuring features

| Channel | Dye | Filter (excitation; nm) | Filter (emission; nm) | Entity component or compartment |
|---|---|---|---|---|
| 1 | Hoechst 33342 | 387/11 | 417-477 | Nucleus |
| 2 | Concanavalin A/ Alexa Fluor 488 conjugate | 472/30a | 503-538a | Endoplasmic reticulum |
| 3 | SYTO 14 green fluorescent nucleic acid stain | 531/40 | 573-613 | Nucleoli, cytoplasmic RNAb |
| 4 | Phalloidin/Alexa Fluor 568 conjugate, wheat-germ agglutinin/Alexa Fluor 555 conjugate | 562/40 | 622-662c | F-actin cytoskelelon, Golgi, plasma membrane |
| 5 | MitoTracker Deep Red | 628/40 | 672-712 | Mitochondria |

Block 412.

Referring to block 412 of FIG. 4A, in some embodiments the distribution metric of the measurement of the different feature across the plurality of test instances of the entity upon exposure of the plurality of test instances of the entity to the respective test perturbation is an arithmetic mean, weighted mean, midrange, midhinge, trimean, Winsorized mean, median, or mode of the different feature across the plurality of test instances of the entity upon exposure of the plurality of test instances of the entity to the respective test perturbation.

Block 414.

Figure 4B:
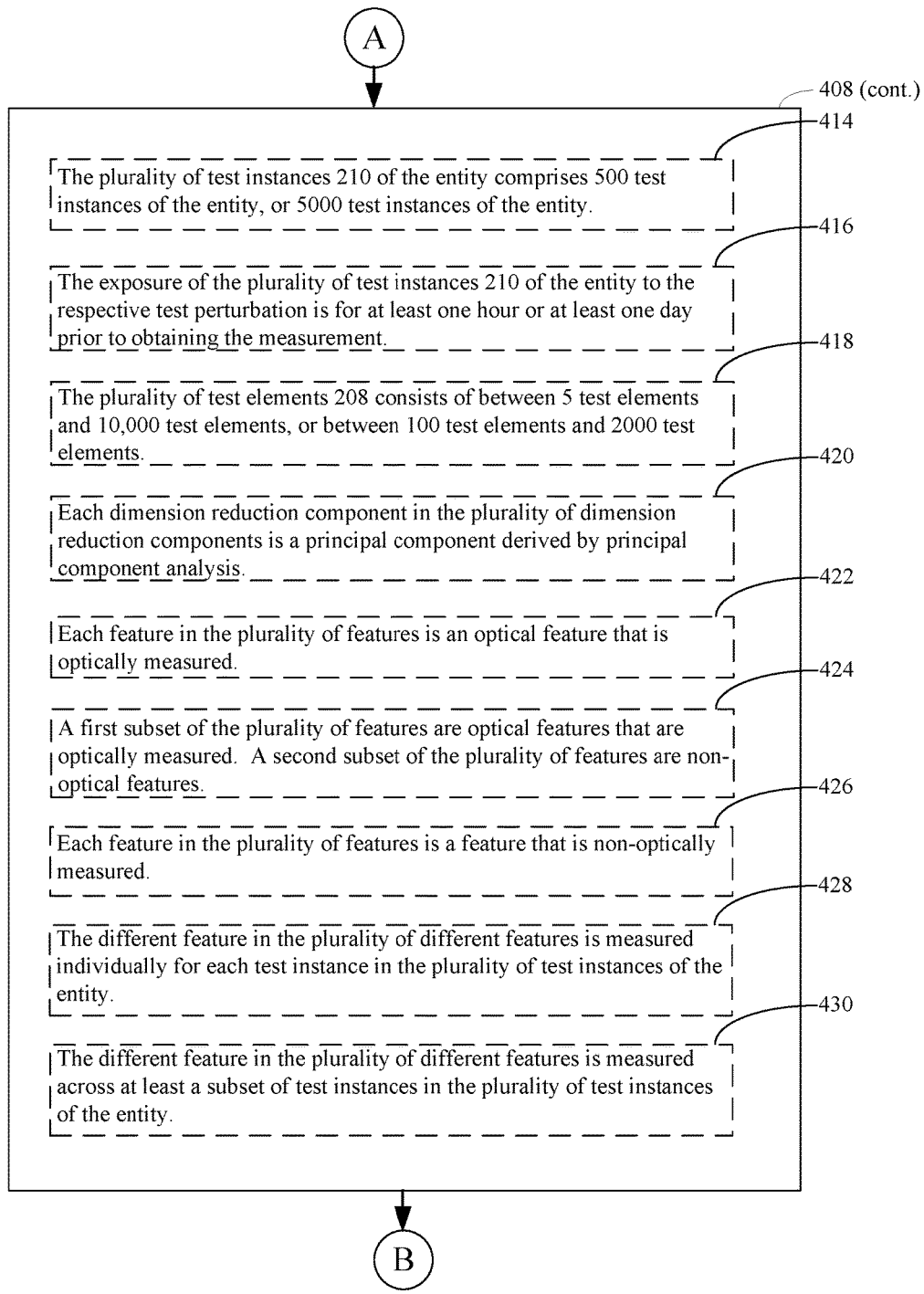

Referring to block 414 of FIG. 4B, in some embodiments, the plurality of test instances 210 of the entity comprises 100 test instances of the entity, 250 test instances of the entity, 400 test instances of the entity, 800 test instances of the entity, 1000 test instances of the entity, 2000 test instances of the entity, 3000 test instances of the entity, 4000 test instances of the entity, 5000 test instances of the entity, 6000 test instances of the entity, 7000 test instances of the entity, or 8000 test instances of the entity. With reference to FIG. 5, this means that in some embodiments, Q is 100 or greater, 250 or greater, 400 or greater, 800 or greater, 1000 or greater, 2000 or greater, 3000 or greater, 4000 or greater, 5000 or greater, 6000 or greater, 7000 or greater, or 8000 greater. In other words, for each respective perturbation in the test set of perturbations, more than 100 test instances of the entity, more than 250 test instances of the entity, more than 400 test instances of the entity, more than 800 test instances of the entity, more than 1000 test instances of the entity, more than 2000 test instances of the entity, more than 3000 test instances of the entity, more than 4000 test instances of the entity, more than 5000 test instances of the entity, more than 6000 test instances of the entity, more than 7000 test instances of the entity, or more than 8000 test instances of the entity are exposed to the respective perturbation and each of the features is measured from these entities upon such perturbation exposure.

Thus, in some such embodiments where the test entity is a cell, the plurality of test instances 210 of the entity comprises 100 test instances of the cell, 250 test instances of the cell, 400 test instances of the cell, 800 test instances of the cell, 1000 test instances of the cell, 2000 test instances of the cell, 3000 test instances of the cell, 4000 test instances of the cell, 5000 test instances of the cell, 6000 test instances of the cell, 7000 test instances of the cell, or 8000 test instances of the cell.

Block 416.

Referring to block 416 of FIG. 4B, in some embodiments, the exposure of the plurality of test instances 210 of the entity to the respective test perturbation is for at least five minutes, at least 20 minutes, at least 30 minutes, at least 45 minutes, at least one hour, at least five hours, at least 10 hours, at least 12 hours, or at least 24 hours prior to obtaining the measurement of features. In some embodiments, the exposure of the plurality of test instances 210 of the entity to the respective test perturbation is between five minutes and two hours prior to obtaining the measurement of the features. In some embodiments, the exposure of the plurality of test instances 210 of the entity to the respective test perturbation is between 30 minutes and five hours prior to obtaining the measurement of the features. In some embodiments, the exposure of the plurality of test instances 210 of the entity to the respective test perturbation is between one hour and 30 hours prior to obtaining the measurement of the features.

Block 418. Referring to block 418 of FIG. 4B, in some embodiments, the plurality of test elements 208 consists of between 5 test elements and 10,000 test elements, between 100 test elements and 5,000 test elements, between 500 test elements and 20,000 test elements, between 25 test elements and 8,000 test elements, between 15 test elements and 10,000 test elements, between 250 test elements and 7,000 test elements, between 100 test elements and 20,000 test elements or between 100 test elements and 2000 test elements.

Block 420. Referring to block 420 of FIG. 4B, in some embodiments where each test element 208 in the plurality of test elements comprises a distribution metric of a respective dimension reduction component in a plurality of dimension reduction components computed using the measurement of the plurality of features across a plurality of test instances of the entity upon exposure of the plurality of test instances of the entity to the respective test perturbation, each dimension reduction component in the plurality of dimension reduction components is a principal component derived by principal component analysis (PCA).

Referring to FIG. 5, PCA reduces the dimensionality of the observed data by transforming the plurality of features 208 to a new set of variables (principal components) that summarize the features of the training set. See, for example, Jolliffe, 1986, Principal Component Analysis, Springer, New York, which is hereby incorporated by reference. PCA is also described in Draghici, 2003, *Data Analysis Tools for DNA Microarrays*, Chapman & Hall/CRC, which is hereby incorporated by reference. Principal components (PCs) are uncorrelated and are ordered such that the $k^{th}$ PC has the $k^{th}$ largest variance among PCs across the observed data for the features. The $k^{th}$ PC can be interpreted as the direction that maximizes the variation of the projections of the data points such that it is orthogonal to the first $k-1$ PCs. The first few PCs capture most of the variation in the observed data. In contrast, the last few PCs are often assumed to capture only the residual "noise" in the observed data. As such, the principal components derived from PCA can serve as the basis of vectors that are used in accordance with the present disclosure. In such an approach, each block 602 in FIG. 6 represents the measurements for the select features for a particular test perturbation and can be considered a vector. As such, FIG. 6 can be viewed as a matrix of vectors, each vector representing a respective perturbation and including measurements for features measured from the respective test entities.

In some embodiments where each test element 208 in the plurality of test elements comprises a distribution metric of a respective dimension reduction component in a plurality of dimension reduction components computed using the measurement of the plurality of features across a plurality of test instances of the entity upon exposure of the plurality of test instances of the entity to the respective test perturbation, the dimension reduction components are derived by a subset selection process. Examples of subset selection methods are disclosed in Hastie et al., 2001, *The Elements of Statistical Learning*, 55-58, which is hereby incorporated by reference.

In some embodiments where each test element 208 in the plurality of test elements comprises a distribution metric of a respective dimension reduction component in a plurality of dimension reduction components computed using the measurement of the plurality of features across a plurality of test instances of the entity upon exposure of the plurality of test instances of the entity to the respective test perturbation, the dimension reduction components are derived by a shrinkage method using a panel of control perturbation. Rather than discarding first features as is the case in subset selection, shrinkage methods impose a penalty on the size of their coefficients. Examples of shrinkage methods are disclosed in Hastie et al., 2001, *The Elements of Statistical Learning*, 59-65, which includes the lasso method, which is hereby incorporated by reference.

Block 422.

Referring to block 422 of FIG. 4B, in some embodiments each feature in the plurality of features is an optical feature that is optically measured. For instance, in some embodiments features are extracted from digital images 106 captured using an epifluorescence microscope (e.g., ImageXpress Micro, Molecular Devices).

In some embodiments, each such feature is a cell morphological features that is measured using computer vision techniques. For instance, in some embodiments each feature is an optical feature that is identified using a cell painting technique. In such embodiments, quantitative data for such features is extracted from microscopy images of entities to identify biologically relevant similarities and differences among samples of entities based on these profiles, where such entities have been exposed to the same or different perturbations. As such, cell painting is a morphological profiling assay that multiplexes a plurality of (e.g., six) fluorescent dyes, imaged in a plurality of (e.g., five) channels, to reveal a plurality of (e.g., eight) broadly relevant cellular components or organelles. Entities are plated in multiwell plates, perturbed with the perturbations to be tested, stained, fixed, and imaged on a high-throughput microscope. Next, automated image analysis software identifies individual entities and measures 1,500 morphological features (e.g., various measures of size, shape, texture, intensity, etc.) to produce a rich profile that is suitable for the detection of subtle phenotypes. See, Bray et al., 2016, "Cell Painting, a high-content image-based assay for morphological profiling using multiplexed fluorescent dyes," Nature Protocols 11(9), 1757-1774, which is hereby incorporated by reference.

In some embodiments, deep learning is used to identify features. For instance, in some embodiments, a plurality of entities, each exposed to the same or different perturbation, are imaged (e.g., at a plurality of different time points) and, for each respective instance of an imaged entity (e.g., at a different time point in the plurality of time points), an image patch within the image (e.g., 27×27 pixels within a two-dimensional digital image) covering the mass-centered body of the entity of the entity (e.g., at the respective time point) is taken. Each such image patch is labeled a particular state based on one or more measured fluorescent signal associated with the image patch thereby resulting in a large number of labeled image patches for a plurality of entities. In some embodiments, these labeled image patches are then subjected to deep learning, such as a combined convolutional neural network with a recurrent neural network (RNN) architecture that automatically extracts local image features and exploits information of the image-patches (e.g., temporal information, changes in fluorescence as a function of perturbation and/or time, etc.). For instance, in some embodiments the deep learning comprises three connected convolutional layers that extract image features. See, for example, Buggenthin et al., 2017, "Prospective identification of hematopoietic lineage choice by deep learning," Nature Methods, 14(4), 403-406, which is hereby incorporated by reference.

Block 424.

Referring to block 424 of FIG. 4B, in some embodiments a first subset of the plurality of features are optical features that are optically measured. A second subset of the plurality of features are non-optical features.

Block 426.

Referring to block 426 of FIG. 4B, in some embodiments each feature in the plurality of features is a feature that is non-optically measured. For instance, in some embodiments, the features are measured using acoustic resonance, electrical impedance, microcantilevers, nanowires or differential calorimetry. See, Cooper, 2006, "Non-optical screening platforms: the next wave in label-free screening?" Drug Discovery Today 11, 1068-1074, which is hereby incorporated by reference. For example, ACEA Biosciences (http://www.aceabio.com) released a real-time cell electronic sensing (RT-CESTM) system, based on a micro-electronic cell sensor array integrated into the bottom of standard Society for Biomolecular Sciences (SBS; http://www.sbsonline.org) format microtitre plates. RT-CES works by measuring electrical impedance across the sensors to detect the presence, absence or change in condition of entities. For entity-based assays, entities are grown in the individual, sensor-containing wells of the microtitre plate and placed in a standard incubator. The system can be programmed to collect feature data as frequently as every minute by sending nominal current through the sensors at the user-defined intervals. The electronic sensors provide information on impedance values, which can be used as feature values directly using the systems and methods of the present disclosure or converted to a measure known as the cell index (the impedance of the cells normalized for the impedance of the media alone) which in turn can be used as a feature in the present disclosure.

Another source of non-optical features that can be used in the present disclosure can be obtained from an Applied BioPhysics (http://www.biophysics.com) slide that has eight or 96 individual wells for cell culturing. The base of the device has an array of gold film electrodes that connect electric cell-substrate impedance sensing (ECIS) electronics to each of the wells. Cell densities ranging from a heavy confluent layer to sparse layers can be measured with this approach. The size of the electrodes restricts the maximum number of anchored cells that can be observed (typically from 100 to 1000 cells). However, by using multiple electrodes in parallel, more surface area in a well can be covered to measure up to 4000 cells. The detection electronics are sufficiently sensitive to detect even a single isolated cell response. In this way, for applications in which the entity is a cell, non-optical features representing cellular behavior in response to perturbations, including cell proliferation, barrier function, attachment and spreading, migration, and invasion under both static and flow conditions can be acquired for use in the systems and methods of the present disclosure. In addition, higher electric fields can be used to measure non-optical features for use in the present disclosure from wound healing assays and, if applied for a shorter duration, to electroporate cells and monitor the subsequent entry of membrane impermeable molecules, such as dsRNA. The technology can also be used to obtain non-optical features in the form of signal transduction, metastatic potential and in vitro toxicity.

Block 428.

Referring to block 428 of FIG. 4B, in some embodiments a different feature in the plurality of different features is measured individually for each test instance in the plurality of test instances of the entity. In other words, all the data needed to quantify a particular instance of a feature is acquired from a single instance of an entity. For example, in the case where the entity is a cell and the feature is cell area, all the data needed to quantify the cell area of a cell is acquired from a single instance of the cell. In order to obtain reliable measurements, and as illustrated in FIG. 2, multiple instances of test entities are measured for this feature, however in embodiments in accordance with block 428, an instance of the feature is measured independently from each of the entities. In some embodiments these individual measurements for a feature for an element of a test vector are combined into a distribution metric as described with reference to block 432 below.

Block 430.

Referring to block 430 of FIG. 4B, in some embodiments a different feature in the plurality of different features is measured across at least a subset of test instances in the plurality of test instances of the entity. In other words, in such embodiments, all the data needed to quantify a particular instance of a feature is acquired from multiple instances of an entity, not from a single entity. For example, in the case where the entity is a cell and the feature is actin content, all the data needed to quantify the cell area of a cell can be acquired across multiple instance of the cell (e.g., all the cells in a particular well of a multiwell plate). In order to obtain reliable measurements, and as illustrated in FIG. 2, multiple instances of test entities are measured for this feature, however in embodiments in accordance with block 430, each instance of the feature is measured independently across a separate plurality of entities. In some embodiments these individual measurements for a feature for an element of a test vector are then combined into a distribution metric as described with reference to block 432 below.

Block 432-434.

Figure 4C:
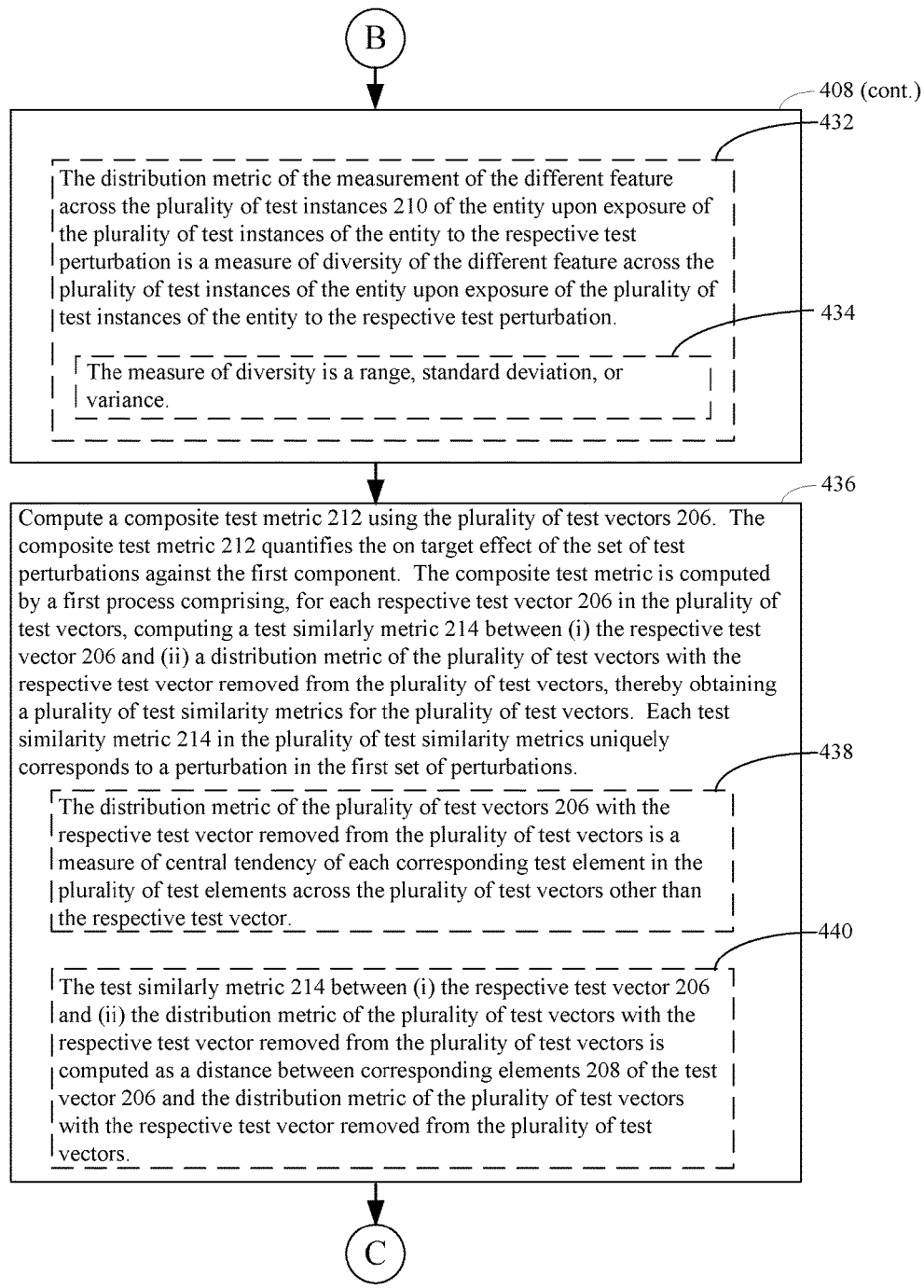

Referring to block 432 of FIG. 4C, it is noted that the test instances of the entities upon exposure to perturbations form the basis for measuring features. As such, for each perturbation, multiple instances of a feature are measured, and these instances of the feature either forms an element of a test vector or contribute to a dimension reduction component that forms an element of a test vector. For instance, in some embodiments, two or more, three or more, four or more, five or more, six or more, between 3 and 10, between 2 and 100, seven or more, or eight or more test instances of the entities are measured for a particular feature upon exposure of such entities to a particular test perturbation. In this way, by taking multiple measurements of a feature a more reliable measurement of each feature in the form of a distribution metric for the feature is obtained. As such, in some embodiments a distribution metric of the measurement of the different feature across the plurality of test instances 210 of the entity upon exposure of the plurality of test instances of the entity to the respective test perturbation is a measure of diversity of the different feature across the plurality of test instances of the entity upon exposure of the plurality of test instances of the entity to the respective test perturbation.

In some such embodiments, referring to block 434 of FIG. 4C, the measure of diversity for a different feature in a plurality of features is a range, standard deviation, or variance of the feature as measured for each test instance of the entity across the plurality of test instances. Likewise, in embodiments where each element in a test vector corresponding to a particular test perturbation is a distribution metric of a respective dimension reduction component in a plurality of dimension reduction components computed using the measurement of the plurality of features across a plurality of test instances of the entity upon exposure of the plurality of test instances of the entity to the particular test perturbation, the measure of diversity for a respective dimension reduction component is a range, standard deviation, or variance of the different dimension reduction component as computed using the component features that contribute to the different dimension reduction component from each test instance of the entity across the plurality of test instances that were exposed to the particular test perturbation.

Blocks 436-438.

Referring to block 436 of FIG. 4C, a composite test metric 212 is computed using the plurality of test vectors 206. The composite test metric 212 quantifies the on target effect of the set of test perturbations against the first component. In some embodiments, the composite test metric is computed by a first process comprising, for each respective test vector 206 in the plurality of test vectors, computing a test similarly metric 214 between (i) the respective test vector 206 and (ii) a distribution metric of the plurality of test vectors with the respective test vector removed from the plurality of test vectors, thereby obtaining a plurality of test similarity metrics for the plurality of test vectors. Each test similarity metric 214 in the plurality of test similarity metrics uniquely corresponds to a perturbation in the first set of perturbations. Thus, to compute the test similarity metric 214 of a first test vector (which represents a test perturbation in the set of test perturbations), the first element of the first test vector is compared to a distribution metric computed across the first element of all other test vectors, excluding the first test vector, the second element of the first test vector is compared to a distribution metric computed across the second element of all other test vectors, excluding the first test vector, and so forth. In other words, a distance is computed between a respective test vector and a reference test vector, where each respective element of the reference test vector is a distribution metric of the respective element across the plurality of test vectors exclusive of the respective test vector. So, for the first test vector, a distance is computed between the first test vector and a reference test vector, where each respective element of the reference test vector is a distribution metric of the respective element across the plurality of test vectors exclusive of the first test vector. Referring to block 438 of FIG. 4C, in some embodiments the distribution metric is a measure of central tendency (an arithmetic mean, weighted mean, midrange, midhinge, trimean, Winsorized mean, median, or mode) of the plurality of test vectors 206 with the respective test vector removed from the plurality of test vectors.

Blocks 440-442.

Referring to block 440 of FIG. 4C, in some embodiments, the test similarly metric 214 between (i) the respective test vector 206 and (ii) the distribution metric (e.g., measure of central tendency) of the plurality of test vectors with the respective test vector removed from the plurality of test vectors is computed as a distance between corresponding elements 208 of the test vector 206 and the distribution metric of the plurality of test vectors with the respective test vector removed from the plurality of test vectors. For instance, in some embodiments, the distance is an angular distance. Referring to block 442, in some embodiments, the distance is an angular distance, for instance, computed as:

$$\frac{\sum_{i}^{n} A_i B_i}{\sqrt{\sum_{i=1}^{n} A_i^2} \sqrt{\sum_{i=1}^{n} B_i^2}}$$

where $A_i$ is a test element i 208 in the respective test vector, $B_i$ is the distribution metric of corresponding test element i in the plurality of test elements 208 across the plurality of test vectors 206 other than the respective test vector, and n is the number of elements in respective test vector (e.g., S elements as illustrated in FIG. 2).

Other similarity measures that can be used to compute the distance between (i) the respective test vector 206 and (ii) the distribution metric of the plurality of test vectors with the respective test vector removed from the plurality of test vectors are discussed in Section 6.7 of Duda and Hart, *Pattern Classification and Scene Analysis,* 1973, John Wiley & Sons, Inc., New York, (hereinafter "Duda 1973"). In some embodiments, rather than using a similarity metric to compute the distance between (i) the respective test vector 206 and (ii) the distribution metric of the plurality of test vectors with the respective test vector removed from the plurality of test vectors a nonmetric similarity function s(x, x') is used to compare the two vectors x (the respective test vector 206) and x' (a vector in which each respective element of the vector is a distribution metric of the respective element in the plurality of test vectors with the respective test vector removed from the plurality of test vectors). Conventionally, s(x, x') is a symmetric function whose value is large when x and x' are somehow "similar." An example of a nonmetric similarity function s(x, x') is provided on page 216 of Duda 1973. For purposes of the present disclosure, the term "test similarly metric" is deemed to encompass similarity metrics, such as the angular distance function of block 442, as well as non-similarity metrics such as those described in Duda 1973.

Block 444.

Referring to block 444 of FIG. 4D, the first process initiated in block 436 of FIG. 4C further comprises computing the composite test metric 212 as a distribution metric such as a measure of central tendency (e.g., arithmetic mean, weighted mean, midrange, midhinge, trimean, Winsorized mean, median, or mode) of the plurality of test similarity metrics 214. In this way, a value, the composite test metric 436, is computed that represents the effect of the entire set of test perturbations.

Block 446.

Referring to block 444 of FIG. 4E, in some embodiments the measure of central tendency of the plurality of test similarity metrics 214 is an arithmetic mean, weighted mean, midrange, midhinge, trimean, Winsorized mean, median, or mode of the plurality of test similarity metrics.

Block 448.

With reference to block 448 of FIG. 4D, a null distribution 216 comprising a plurality of composite control metrics 218 is computed in order to calibrate the composite test metric. While each of the test vectors that were ultimately used to compute the composite test metric 212 were based upon perturbation of a target first component, the null distribution is built upon perturbations that are intendent to target random components of the entity under consideration. In this way, the null distribution provides a statistical basis for determining the relevance of the computed value of the composite test metric 212.

In some embodiments each respective composite control metric 218 in the plurality of composite control metrics is computed by a second process comprising selecting a respective set of control perturbations 220 from a plurality of perturbations. Each control perturbation 222 in the respective set of control perturbations 220 is against a different component 224 in the plurality of components.

Block 450.

With reference to block 450 of FIG. 4D, in some embodiments, the plurality of composite control metrics 218 comprises 50 composite control metrics 218, 100 composite control metrics 218, 500 composite control metric 218, 1000 composite control metrics, or 2000 composite control metrics, where each composite control metric represents a different set of control perturbations from the plurality of perturbations.

Block 452. With reference to block 452 of FIG. 4D, in some embodiments, the respective set of control perturbations 220 for a particular composite control metrics 218 in the plurality of composite control metrics consists of between 2 and 12 different control perturbations 222, between 3 and 10 different control perturbations 222, between 5 and 15 different control perturbations 222, between 6 and 60 different control perturbation, or between 3 and 300 different control perturbations 222. In some embodiments, a control perturbation is a small interfering RNA (siRNA) that specifically recognizes a component in an entity. Each siRNA is a double-stranded RNA molecule, 20-25 base pairs in length that interferes with the expression of a specific gene with a complementary nucleotide sequence by degrading mRNA after transcription preventing translation of the gene. See, Agrawal et al., 2003, "RNA interference: biology, mechanism, and applications," Microbiol Mol Biol Rev. 67: 657, which is hereby incorporated by reference.

Block 454.

With reference to block 454 of FIG. 4E, in some embodiments, the second process further comprises obtaining, for each respective control perturbation 222 in the respective set of control perturbations 220, a corresponding control vector 226, thereby obtaining a respective plurality of control vectors. Each corresponding control vector 226 comprises a plurality of control elements 228.

In some embodiments, each control element 228 in the plurality of control elements 228 comprises a distribution metric of a measurement of a different feature, in the plurality of features, across a respective plurality of control instances 230 of the entity upon exposure of the respective plurality of control instances of the entity to the respective control perturbation 222.

In some embodiments such data is acquired using an automated cellular imaging system (e.g., ImageXpress Micro, Molecular Devices), where entities have been arranged in multiwell plates (e.g., 384-well plates) after they have been stained with a panel of dyes that emit at different discrete wavelengths (e.g., Hoechst 33342, Alexa Fluor 594 phalloidin, etc.) and a control perturbation. In some embodiments the entities are imaged with an exposure that is a determined by the marker dye used (e.g., 15 ms for Hoechst, 1000 ms for phalloidin), at 20× magnification with 2x binning. For each well, in some embodiments the optimal focus is found using laser auto-focusing on a particular dye channel (e.g., the Hoechst channel). In some embodiments the automated microscope was then programmed to collect a z-stack of 32 images (z=0 at the optimal focal plane, 16 images above the focal plane, 16 below) with 2 μm between slices. In some embodiments each well contains several thousand entities in them, and thus each digital representation of a well captured by a cameral represents several thousand entities in each of several different wells. In some embodiments, segmentation software is used to identify individual entities in the digital images and moreover various components (e.g., cellular components) within individual entities. Once the cellular components are segmented and identified mathematical transformations are performed on these components on order to obtain the measurements of features.

As such, to illustrate, in the case where the set of control perturbations 220 for a given composite control metric 218 is five control perturbations 222, there will be five control vectors 226, that is, a control vector 226 for each control perturbation in the set of five control perturbations 220 for the given composite control metric. Moreover, each control vector 226 will comprise a plurality of control elements 228, (e.g. five or more control elements 228, ten or more control elements 228, twenty or more control elements 228, 100 or more control elements 228, or one thousand or more control elements 228). Each control element 228 in a control vector 226 represents a different feature in a plurality of features that is measured from control instances of the control entity 230 upon exposure to the control perturbation. In typical embodiments, the set of features that is measured for each of the control vectors 226 is the same features that is measured for each of the test vectors 206.

To further illustrate, consider the case of a first control vector 226 corresponding to a first control perturbation 222, where the first control vector 226 comprises twenty control elements 228. Each control element 228 represents a different feature that is measured from control instances of the entity upon exposure to the first control perturbation 222. For instance, the first control element 228 in the first control vector 226 represents the measurement of the first feature in each of a plurality of control instances 230 of the entity upon exposure to the first perturbation. More specifically, each control element 228 represents a distribution metric of a corresponding feature that is measured from each of the control instances 230 of the control entity upon exposure to a control perturbation 222 corresponding to the control vector 226 that contains the control element 228.

In typical embodiments, the entities that are exposed to test perturbations in order to form the test vectors 206 are the same type of entities that are exposed to control perturbations 222 to form the control vectors 226.

The measurement of the plurality of features across a plurality of control instances of the entity upon exposure of the plurality of control instances of the entity to a respective control perturbation 222 in the plurality of perturbations for a composite control metric 218 results in an N-dimensional space, where each integer in the N-dimensional space is a different feature in the plurality of features.

In some alternative embodiments, each control element 228 in the plurality of control elements for a control vector 226 comprises a distribution metric of a respective dimension reduction component in a plurality of dimension reduction components, where the dimension reduction components were identified as set forth in block 408 using the measurement of the plurality of features across a plurality of control instances of the entity upon exposure of the plurality of test instances of the entity to a respective control perturbation. Such embodiments are advantageous because they eliminate or reduce redundancy between highly correlated feature like size, area of the nucleus and perimeter of the nucleus of an entity. Thus, in such embodiments, the plurality of features 226 (N features) across the plurality of control instances 230 of the entity upon exposure of the plurality of control instances of the entity to a control perturbation are used to populate the plurality of dimension reduction components for a given control element 228 of a control vector 226. Thus, in a case where the set of features is one thousand features, there will be less than five hundred dimension reduction components in a control vector. In such instances, each respective control vector 226 will represent a control perturbation 222 in the set of control perturbations 220 of a composite control metric 218 and each respective control element 228 of each respective control vector 226 will include a value for a corresponding dimension reduction component based on the values of the features represented by the dimension reduction component across the control entities that have been exposed to the control perturbation 222 that corresponds to the respective control vector 226.

Block 456. With reference to block 456 of FIG. 4E, in some embodiments, the respective plurality of control instances 230 of the entity comprises 100 control instances of the entity, 250 control instances of the entity, 400 control instances of the entity, 800 control instances of the entity, 1000 control instances of the entity, 2000 control instances of the entity, 3000 control instances of the entity, 4000 control instances of the entity, 5000 control instances of the entity, 6000 control instances of the entity, 7000 control instances of the entity, or 8000 control instances of the entity. In other words, for each respective control perturbation 222 in a set of control perturbations 220, more than 100 control instances of the entity, more than 250 control instances of the entity, more than 400 control instances of the entity, more than 800 control instances of the entity, more than 1000 control instances of the entity, more than 2000 control instances of the entity, more than 3000 control instances of the entity, more than 4000 control instances of the entity, more than 5000 control instances of the entity, more than 6000 control instances of the entity, more than 7000 control instances of the entity, or more than 8000 control instances of the entity are exposed to the respective control perturbation and each of the features is measured from these entities upon such perturbation exposure.

Thus, in some such embodiments where the control entity is a cell, the plurality of control instances 230 of the entity comprises 100 control instances of the cell, 250 control instances of the cell, 400 control instances of the cell, 800 control instances of the cell, 1000 control instances of the cell, 2000 control instances of the cell, 3000 control instances of the cell, 4000 control instances of the cell, 5000 control instances of the cell, 6000 control instances of the cell, 7000 control instances of the cell, or 8000 control instances of the cell.

Block 458. With reference to block 458 of FIG. 4E, in preferred embodiments the respective plurality of control instances 230 of the entity are exposed to respective control perturbations 222 for the same amount of time that the test instances 210 were exposed to test perturbations in block 416. Accordingly, in some embodiments, the exposure of the plurality of control instances 230 of the entity to the respective control perturbation 222 is for at least five minutes, at least 20 minutes, at least 30 minutes, at least 45 minutes, at least one hour, at least five hours, at least 10 hours, at least 12 hours, or at least 24 hours prior to obtaining the measurement of features. In some embodiments, the exposure of the plurality of control instances 230 of the entity to the respective control perturbation 222 is between five minutes and two hours prior to obtaining the measurement of the features. In some embodiments, the exposure of the plurality of control instances 230 of the entity to the respective control perturbation 222 is between 30 minutes and five hours prior to obtaining the measurement of the features. In some embodiments, the exposure of the plurality of control instances 230 of the entity to the respective control perturbation 222 is between one hour and 30 hours prior to obtaining the measurement of the features.

Blocks 460-461.

It is noted that the control instances of the entities upon exposure to perturbations form the basis for measuring features for each of the composite control metrics 218. As such, for each control perturbation 222, multiple instances of a feature are measured, and these instances of the feature either forms a control element 228 of a control vector 226 directly or contribute to a dimension reduction component that forms the control element. For instance, in some embodiments, two or more, three or more, four or more, five or more, six or more, between 3 and 10, between 2 and 100, seven or more, or eight or more test instances of the entities are measured for a particular feature upon exposure of such entities to a particular control perturbation. In this way, by taking multiple measurements of a feature, a more reliable measurement of each feature in the form of a distribution metric for the feature is obtained. In some embodiments, the distribution metric is an arithmetic mean, weighted mean, midrange, midhinge, trimean, Winsorized mean, median, or mode of the different feature across the plurality of control instances of the entity upon exposure of the plurality of control instances 230 of the entity to the respective control perturbation 222.

In some embodiments, referring to block 461 of FIG. 4E, the measurement of the different feature across the plurality of control instances 230 of the entity upon exposure of the plurality of control instances of the entity to the respective control perturbation 222 is a measure of diversity of the different feature across the plurality of control instances of the entity upon exposure of the plurality of control instances of the entity to the respective control perturbation. In some embodiments, this measure of diversity is a range, standard deviation, or variance of the feature as measured for each control instance 230 of the entity across the plurality of control instances for the particular control perturbation 222. Likewise, in embodiments where each element 228 in a control vector 226 corresponding to a particular control perturbation 222 is a distribution metric of a respective dimension reduction component in a plurality of dimension reduction components computed using the measurement of the plurality of features across a plurality of control instances of the entity upon exposure to the particular control perturbation, the measure of diversity is a range, standard deviation, or variance of the different dimension reduction component as computed using the component features that contribute to the different dimension reduction component from each control instance of the entity across the plurality of control instances that were exposed to the particular control perturbation.

Blocks 462-464.

Figure 4F:
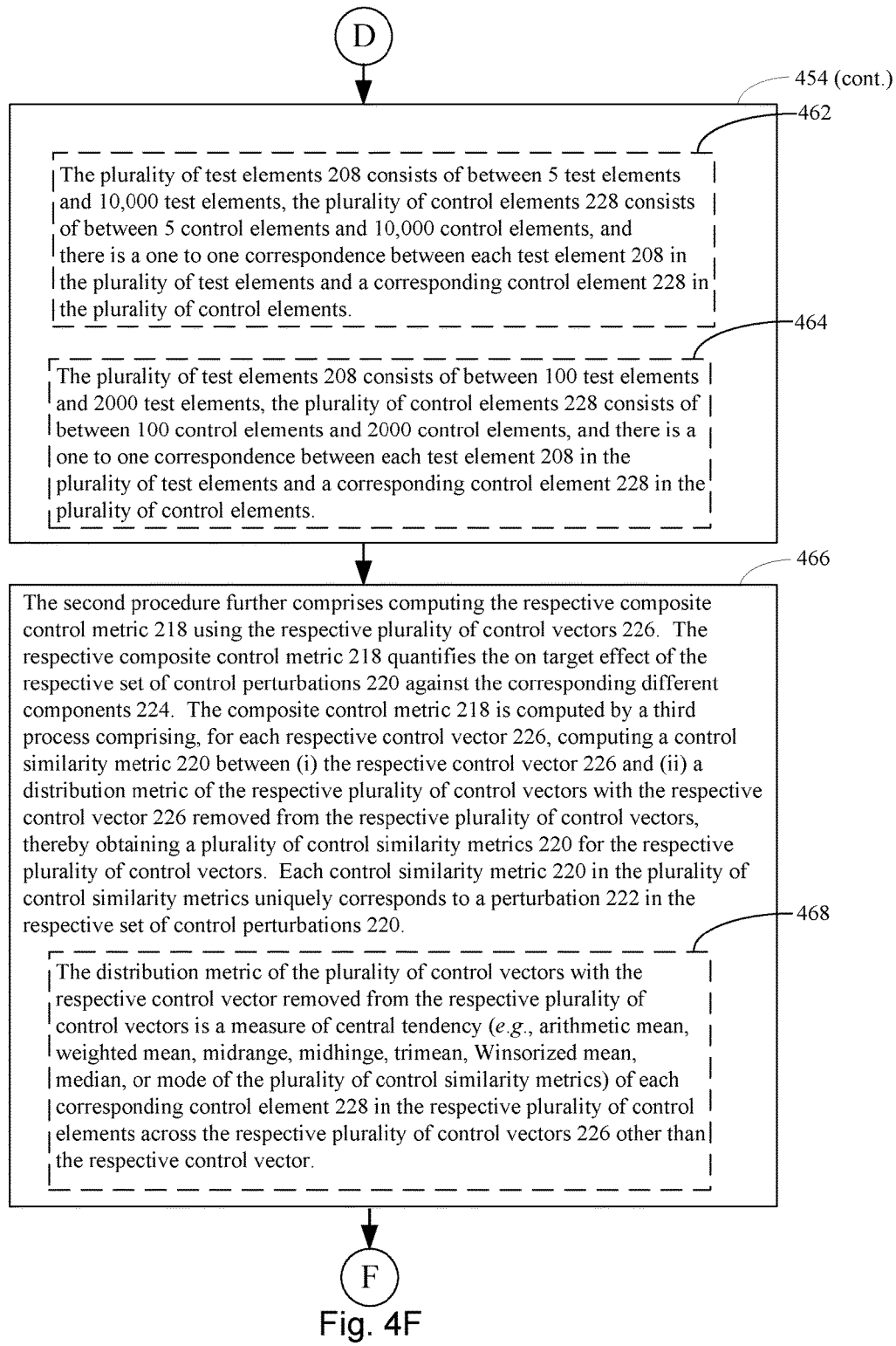

With reference to block 462 of FIG. 4F, in some embodiments, the plurality of test elements 208 consists of between 5 test elements and 10,000 test elements, the plurality of control elements 228 consists of between 5 control elements and 10,000 control elements, and there is a one to one correspondence between each test element 208 in the plurality of test elements and a corresponding control element 228 in the plurality of control elements. That is, in such embodiments, each test vector has the same number of elements as each control vector. For instance, in such embodiments, if there are 100 test elements in each test vector, then there are 100 control elements in each control vector. However, the test elements are the result of measurements using a test perturbation that affects the first component of the entity while the control elements are the result of measuring using a control perturbation that affects a component of the entity other than the first component. With reference to block 464 of FIG. 4F, in some embodiments, the plurality of test elements 208 consists of between 100 test elements and 2000 test elements, the plurality of control elements 228 consists of between 100 control elements and 2000 control elements, and there is a one to one correspondence between each test element 208 in the plurality of test elements and a corresponding control element 228 in the plurality of control elements.

Blocks 466-468.

With reference to block 466 of FIG. 4F, the second procedure further comprises computing a respective composite control metric 218 using the respective plurality of control vectors 226 that corresponds to the control metric 218 as illustrated in FIG. 3. The respective composite control metric 218 quantifies the on target effect of the respective set of control perturbations 220 against the corresponding different components 224 targeted by the set of control perturbations 220 associated with the composite control metric.

In some embodiments, the respective composite control metric 218 is computed by a third process comprising, for each respective control vector 226 for the respective composite control metric 218, computing a control similarity metric 219 between (i) the respective control vector 226 and (ii) a distribution metric of the respective plurality of control vectors with the respective control vector 226 removed from the respective plurality of control vectors, thereby obtaining a plurality of control similarity metrics 219 for the respective plurality of control vectors. Each control similarity metric 219 in the plurality of control similarity metrics uniquely corresponds to a perturbation 222 in the respective set of control perturbations 220. Thus, to compute the control similarity metric 219 of a first control vector (which represents a control perturbation 222 in the set of control perturbations 220 for a respective composite control metric 218), the first element 228 of the first control vector 226 is compared to a distribution metric computed across the first element of all other control vectors associated with the respective composite control metric 218, excluding the first control vector, the second element of the first control vector is compared to a distribution metric computed across the second element of all other control vectors associated with the respective composite control metric 228, excluding the first control vector, and so forth. In other words, a distance is computed between a respective control vector and a reference control vector, where each respective element of the reference control vector is a distribution metric of the respective element across the plurality of control vectors associated with the respective composite control metric 218 exclusive of the respective control vector. So, for the first control vector, a distance is computed between the first control vector and a reference control vector, where each respective element of the reference control vector is a distribution metric of the respective element across the plurality of control vectors associated with the respective composite control metric 218 exclusive of the first control vector. With reference to block 468 of FIG. 4F, in some embodiments, the distribution metric is a measure of central tendency (an arithmetic mean, weighted mean, midrange, midhinge, trimean, Winsorized mean, median, or mode) of each corresponding control element 228 in the respective plurality of control elements across the respective plurality of control vectors 226 associated with the respective control metric 218 other than the respective control vector with the respective control vector 226 removed from the plurality of control vectors.

Blocks 470-472.

With reference to block 470 of FIG. 4F, in some embodiments, the control similarly metric 219 between (i) the respective control vector 226 and (ii) the distribution metric of the respective plurality of control vectors associated with a respective composite control metric 218 with the respective control vector removed from the respective plurality of control vectors is computed as a distance between corresponding elements of the respective control vector and the distribution metric of the respective plurality of control vectors with the respective control vector removed from the respective plurality of control vectors. In some embodiments the distance is an angular distance. For instance, with reference to block 472 of FIG. 4G, in some embodiments the distance is an angular distance computed as $$\frac{\sum_{i}^{n} A_i B_i}{\sqrt{\sum_{i=1}^{n} A_i^2} \sqrt{\sum_{i=1}^{n} B_i^2}}$$

where $A_i$ is a control element i in the respective control vector, $B_i$ is the distribution metric of corresponding control element i in the plurality of control elements across the respective plurality of control vectors other than the respective control vector, and n is the number of elements in respective control vector.

Other similarity measures that can be used to compute the distance between (i) the respective control vector 226 and (ii) the distribution metric of the plurality of control vectors with the respective control vector removed are discussed in Section 6.7 of Duda and Hart, *Pattern Classification and Scene Analysis*, 1973, John Wiley & Sons, Inc., New York, (hereinafter "Duda 1973"). In some embodiments, rather than using a similarity metric to compute the distance between (i) the respective control vector 226 and (ii) the distribution metric of the plurality of test vectors with the respective test vector removed, a nonmetric similarity function s(x, x') is used to compare the two vectors x (the respective control vector 226) and x' (a vector in which each respective element of the vector is a distribution metric of the respective element in the plurality of control vectors with the respective control vector removed). Conventionally, s(x, x') is a symmetric function whose value is large when x and x' are somehow "similar." An example of a nonmetric similarity function s(x, x') is provided on page 216 of Duda 1973. For purposes of the present disclosure, the term "test similarly metric" is deemed to encompass similarity metrics, such as the angular distance function of block 472, as well as non-similarity metrics such as those described in Duda 1973.

Block 474.

Figure 4G:
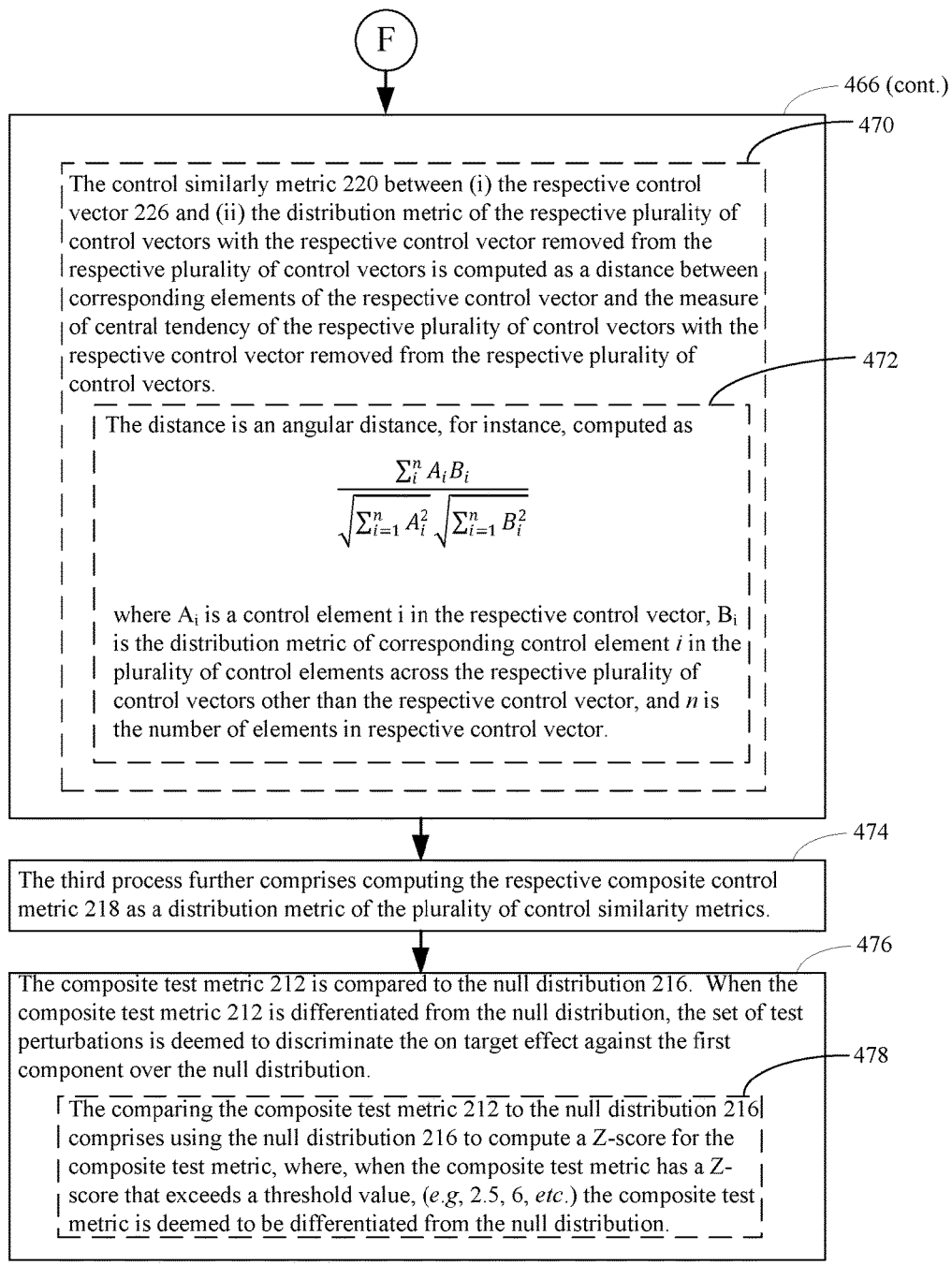

With reference to block 474 of FIG. 4G, in some embodiments, the third process further comprises computing the respective composite control metric 218 as a distribution metric, such as a measure of central tendency (e.g., arithmetic mean, weighted mean, midrange, midhinge, trimean, Winsorized mean, median, or mode) of the plurality of control similarity metrics associated with the respective composite control metric.

Blocks 476-478.

With reference to block 476 of FIG. 4G, in some embodiments, the composite test metric 212 is compared to the null distribution 216. When the composite test metric 212 is differentiated from the null distribution, the set of test perturbations is deemed to discriminate the on target effect against the first component over the null distribution. With reference to block 478 of FIG. 4G, in some embodiments, this comparison of the composite test metric 212 to the null distribution 216 comprises using the null distribution 216 to compute a Z-score for the composite test metric. When the composite test metric has a Z-score that exceeds a threshold value, (e.g, 2.5, 6, etc.) the composite test metric is deemed to be differentiated from the null distribution. A z-score is the number of standard deviations from the mean a data point is. As such, it is a measure of how many standard deviations the composite test metric 212 is above the population mean, as represented by the null distribution 216. A z-score is also known as a standard score and it can be placed on a normal distribution curve. In order to compute the z-score, the mean μ of the composite control metrics and the standard deviation σ of the composite control metrics 218 is computed. In some embodiments, the z score formula for the composite test metric is:

$$z=(x-\mu)/\alpha$$

where x is the composite test metric, μ is the mean of the plurality of composite control metrics 218, and σ is the standard deviation of the plurality of composite control metrics 218.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIGS. 1, 2, 3, and/or described in FIG. 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A computer system for determining whether a set of test chemical compositions discriminates over a null distribution for an on target effect against a first gene of a cell, wherein the set of test chemical compositions comprises a plurality of test chemical compositions against the first gene and the cell comprises a plurality of genes including the first gene, the computer system comprising:
 one or more processors;
 a memory; and
 one or more programs, wherein the one or more programs are stored in the memory and are configured to be executed by the one or more processors, the one or more programs including instructions for:
 (A) obtaining, for each respective test chemical composition in the set of test chemical compositions, a corresponding test vector, thereby obtaining a plurality of test vectors, wherein each corresponding test vector comprises a plurality of test elements, each test element in the plurality of test elements comprising a test distribution metric of a respective dimension reduction component in a plurality of dimension reduction components computed using a measurement of a plurality of features across a plurality of test instances of the cell upon exposure of the plurality of test instances of the cell to the respective test chemical composition, wherein the plurality of dimension reduction components of the test distribution metric is less than the plurality of features;
 (B) computing a composite test metric, using the plurality of test vectors, wherein the composite test metric quantifies the on target effect of the set of test chemical compositions against the first gene, and wherein the composite test metric is computed by a first process comprising:
 (a) for each respective test vector in the plurality of test vectors, computing a test similarly metric between (i) the respective test vector and (ii) a distribution metric of the plurality of test vectors with the respective test vector removed from the plurality of test vectors, thereby obtaining a plurality of test similarity metrics for the plurality of test vectors, each test similarity metric in the plurality of test similarity metrics uniquely corresponding to a chemical composition in the first set of chemical compositions, and
 (b) computing the composite test metric as a measure of central tendency of the plurality of test similarity metrics;
 (C) computing the null distribution, wherein the null distribution comprises a plurality of composite control metrics, each respective composite control metric in the plurality of composite control metrics computed by a second process comprising:
 (a) selecting a respective set of control chemical compositions from a plurality of chemical compositions, wherein each control chemical composition in the respective set of control chemical compositions is against a different gene in the plurality of genes;
 (b) obtaining, for each respective control chemical composition in the respective set of control chemical compositions, a corresponding control vector, thereby obtaining a respective plurality of control vectors, wherein each corresponding control vector comprises a plurality of control elements, each control element in the plurality of control elements comprising a control distribution metric of a respective dimension reduction component in a plurality of dimension reduction components computed using a measurement of the plurality of features across a respective plurality of control instances of the cell upon exposure of the respective plurality of control instances of the cell to the respective control chemical composition, wherein the plurality of dimension reduction components of the control distribution metric is less than the plurality of features;
 (c) computing the respective composite control metric, using the respective plurality of control vectors, wherein the respective control metric quantifies the on target effect of the respective set of control chemical compositions against the corresponding different gene, and wherein the control metric is computed by a third process comprising:
 (1) for each respective control vector, computing a control similarity metric between (i) the respective control vector and (ii) a distribution metric of the respective plurality of control vectors with the respective control vector removed from the respective plurality of control vectors, thereby obtaining a plurality of control similarity metrics for the respective plurality of control vectors, each control similarity metric in the plurality of control similarity metrics uniquely corresponding to a chemical composition in the respective set of control chemical compositions, and (2) computing the respective composite control metric as a distribution metric of the plurality of control similarity metrics; and (D) comparing the composite test metric to the null distribution, wherein when the composite test metric is differentiated from the null distribution, the set of test chemical compositions is deemed to discriminate the on target effect against the first gene over the null distribution.

2. The computer system of claim 1, wherein the different feature is selected from the plurality of features, each feature in the plurality of features representing a color, texture, or size of the cell or an enumerated portion of the cell upon exposure of the cell to the respective test chemical compositions or control chemical compositions.

3. The computer system of claim 1, wherein the set of test chemical compositions consists of between 3 and 300 different test chemical compositions.

4. The computer system of claim 1, wherein each test chemical composition in the set of test chemical compositions further has an off target effect against one or more genes in the plurality of genes other than the first gene.

5. The computer system of claim 1, wherein the plurality of test instances of the cell comprises 500 test instances of the cell.

6. The computer system of claim 1, wherein the exposure of the plurality of test instances of the cell to the respective test chemical composition is for at least one hour prior to obtaining the measurement.

7. The computer system of claim 1, wherein the plurality of test elements consists of between 5 test elements and 10,000 test elements.

8. The computer system of claim 1, wherein the distribution metric of the plurality of test vectors with the respective test vector removed from the plurality of test vectors is a measure of central tendency of each corresponding test element in the plurality of test elements across the plurality of test vectors other than the respective test vector.

9. The computer system of claim 8, wherein the test similarly metric between (i) the respective test vector and (ii) the distribution metric of the plurality of test vectors with the respective test vector removed from the plurality of test vectors is computed as a distance between corresponding elements of the test vector and the distribution metric of the plurality of test vectors with the respective test vector removed from the plurality of test vectors.

10. The computer system of claim 9, wherein the distance is an angular distance computed as:

$$\frac{\sum\limits_{i}^{n} A_i B_i}{\sqrt{\sum\limits_{i=1}^{n} A_i^2} \sqrt{\sum\limits_{i=1}^{n} B_i^2}}$$

and wherein,
$A_i$ is a test element i in the respective test vector,
$B_1$ is the distribution metric of corresponding test element i in the plurality of test elements across the plurality of test vectors other than the respective test vector, and
n is the number of elements in respective test vector.

11. The computer system of claim 1, wherein the measure of central tendency of the plurality of test similarity metrics is an arithmetic mean, weighted mean, midrange, midhinge, trimean, Winsorized mean, median, or mode of the plurality of test similarity metrics.

12. The computer system of claim 1, wherein the plurality of composite control metrics comprises 100 composite control metrics, each composite control metric representing a different combination of control chemical composition from the plurality of chemical compositions.

13. The computer system of claim 1, wherein the respective set of control chemical compositions consists of between 3 and 300 different control chemical compositions.

14. The computer system of claim 1, wherein the respective plurality of control instances of the cell comprises 1000 control instances of the cell.

15. The computer system of claim 1, wherein the exposure of the respective plurality of control instances of the cell to the respective control chemical composition is for at least one hour prior to obtaining the measurement.

16. The computer system of claim 1, wherein
the plurality of test elements consists of between 5 test elements and 10,000 test elements,
the plurality of control elements consists of between 5 control elements and 10,000 control elements, and
there is a one to one correspondence between each test element in the plurality of test elements and a corresponding control element in the plurality of control elements.

17. The computer system of claim 1, wherein
the plurality of test elements consists of between 100 test elements and 2000 test elements,
the plurality of control elements consists of between 100 control elements and 2000 control elements, and
there is a one to one correspondence between each test element in the plurality of test elements and a corresponding control element in the plurality of control elements.

18. The computer system of claim 1, wherein the distribution metric of the plurality of control vectors with the respective control vector removed from the respective plurality of control vectors is a measure of central tendency of each corresponding control element in the respective plurality of control elements across the respective plurality of control vectors other than the respective control vector.

19. The computer system of claim 18, wherein the measure of central tendency of each corresponding control element in the respective plurality of control elements across the respective plurality of control vectors other than the respective control vector is an arithmetic mean, weighted mean, midrange, midhinge, trimean, Winsorized mean, median, or mode of the plurality of control similarity metrics.

20. The computer system of claim 18, wherein the control similarly metric between (i) the respective control vector and (ii) the distribution metric of the respective plurality of control vectors with the respective control vector removed from the respective plurality of control vectors is computed as a distance between corresponding elements of the respective control vector and the distribution metric of the respective plurality of control vectors with the respective control vector removed from the respective plurality of control vectors.

21. The computer system of claim 20, wherein the distance is an angular distance computed as:

$$\frac{\sum_{i}^{n} A_i B_i}{\sqrt{\sum_{i=1}^{n} A_i^2} \sqrt{\sum_{i=1}^{n} B_i^2}}$$

wherein,
$A_i$ is a control element i in the respective control vector,
$B_i$ is the distribution metric of corresponding control element i in the plurality of control elements across the respective plurality of control vectors other than the respective control vector, and
n is the number of elements in respective control vector.

22. The computer system of claim 1, wherein the comparing the composite test metric to the null distribution comprises:
using the null distribution to compute a Z-score for the composite test metric,
wherein, when the composite test metric has a Z-score that exceeds a threshold value, the composite test metric is deemed to be differentiated from the null distribution.

23. The computer system of claim 1, wherein each dimension reduction component in the plurality of dimension reduction components is a principal component derived by principal component analysis.

24. The computer system of claim 1, wherein each feature in the plurality of features is an optical feature that is optically measured.

25. The computer system of claim 1, wherein
a first subset of the plurality of features are optical features that are optically measured; and
a second subset of the plurality of features are non-optical features.

26. The computer system of claim 1, wherein each feature in the plurality of features is a feature that is non-optically measured.

27. A method for determining whether a set of test chemical compositions discriminates over a null distribution for an on target effect against a first gene of a cell, wherein the set of test chemical compositions comprises a plurality of test chemical compositions against the first gene and the cell comprises a plurality of genes including the first gene, the method comprising:
at a computer system comprising a processor and a memory:
(A) obtaining, for each respective test chemical composition in the set of test chemical compositions, a corresponding test vector, thereby obtaining a plurality of test vectors, wherein each corresponding test vector comprises a plurality of test elements, each element in the plurality of test elements comprising a test distribution metric of a respective dimension reduction component in a plurality of dimension reduction components computed using a measurement of a plurality of features across a plurality of test instances of the cell upon exposure of the plurality of test instances of the cell to the respective test chemical composition wherein the plurality of dimension reduction components of the test distribution metric is less than the plurality of features;
(B) computing a composite test metric, using the plurality of test vectors, wherein the composite test metric quantifies the on target effect of the set of test chemical compositions against the first gene, and wherein the composite test metric is computed by a first process comprising:
(a) for each respective test vector in the plurality of test vectors, computing a test similarly metric between (i) the respective test vector and (ii) a measure of central tendency of the plurality of test vectors with the respective test vector removed from the plurality of test vectors, thereby obtaining a plurality of test similarity metrics for the plurality of test vectors, each test similarity metric in the plurality of test similarity metrics uniquely corresponding to a chemical composition in the first set of chemical compositions, and
(b) computing the composite test metric as a measure of central tendency of the plurality of test similarity metrics;
(C) computing the null distribution, wherein the null distribution comprises a plurality of composite control metrics, each respective composite control metric in the plurality of composite control metrics computed by a second process comprising:
(a) selecting a respective set of control chemical compositions from a plurality of chemical compositions, wherein each control chemical composition in the respective set of control chemical compositions is against a different gene in the plurality of genes;
(b) obtaining, for each respective control chemical composition in the respective set of control chemical compositions, a corresponding control vector, thereby obtaining a respective plurality of control vectors, wherein each corresponding control vector comprises a plurality of control elements, each control element in the plurality of control elements comprising a control distribution metric of a respective dimension reduction component in a plurality of dimension reduction components computed using a measurement of the plurality of features across the respective plurality of control instances of the cell upon exposure of the respective plurality of control instances of the cell to the respective control chemical composition, wherein the plurality of dimension reduction components of the control distribution metric is less than the plurality of features;
(c) computing the respective composite control metric, using the respective plurality of control vectors, wherein the respective control metric quantifies the on target effect of the respective set of control chemical compositions against the corresponding different gene, and wherein the control metric is computed by a third process comprising:
(1) for each respective control vector, computing a control similarity metric between (i) the respective control vector and (ii) a measure of central tendency of the respective plurality of control vectors with the respective control vector removed from the respective plurality of control vectors, thereby obtaining a plurality of control similarity metrics for the respective plurality of control vectors, each control similarity metric in the plurality of control similarity metrics uniquely corresponding to a chemical composition in the respective set of control chemical compositions, and (2) computing the respective composite control metric as a measure of central tendency of the plurality of control similarity metrics; and (D) comparing the composite test metric to the null distribution, wherein when the composite test metric is differentiated from the null distribution, the set of test chemical compositions is deemed to discriminate the on target effect against the first gene over the null distribution.

28. A nontransitory computer readable storage medium and one or more computer programs embedded therein for determining whether a set of test chemical compositions discriminates over a null distribution for an on target effect against a first gene of cell, wherein the set of test chemical compositions comprises a plurality of test chemical compositions against the first gene and the cell comprises a plurality of genes including the first gene, the one or more computer programs comprising instructions which, when executed by a computer system, cause the computer system to perform a method comprising:

(A) obtaining, for each respective test chemical composition in the set of test chemical compositions, a corresponding test vector, thereby obtaining a plurality of test vectors, wherein each corresponding test vector comprises a plurality of test elements, each test element in the plurality of test elements comprising a test distribution metric of a respective dimension reduction component in a plurality of dimension reduction components computed using a measurement of a plurality of features across a plurality of test instances of the cell upon exposure of the plurality of test instances of the cell to the respective test chemical composition, wherein the plurality of dimension reduction components of the test distribution metric is less than the plurality of features;

(B) computing a composite test metric, using the plurality of test vectors, wherein the composite test metric quantifies the on target effect of the set of test chemical compositions against the first gene, and wherein the composite test metric is computed by a first process comprising:

(a) for each respective test vector in the plurality of test vectors, computing a test similarly metric between (i) the respective test vector and (ii) a measure of central tendency of the plurality of test vectors with the respective test vector removed from the plurality of test vectors, thereby obtaining a plurality of test similarity metrics for the plurality of test vectors, each test similarity metric in the plurality of test similarity metrics uniquely corresponding to a chemical composition in the first set of chemical compositions, and (b) computing the composite test metric as a measure of central tendency of the plurality of test similarity metrics;

(C) computing the null distribution, wherein the null distribution comprises a plurality of composite control metrics, each respective composite control metric in the plurality of composite control metrics computed by a second process comprising:

(a) selecting a respective set of control chemical compositions from a plurality of chemical compositions, wherein each control chemical composition in the respective set of control chemical compositions is against a different gene in the plurality of genes;

(b) obtaining, for each respective control chemical composition in the respective set of control chemical compositions, a corresponding control vector, thereby obtaining a respective plurality of control vectors, wherein each corresponding control vector comprises a plurality of control elements, each control element in the plurality of control elements comprising a control distribution metric of a respective dimension reduction component in a plurality of dimension reduction components computed using a measurement of the plurality of features across a respective plurality of control instances of the cell upon exposure of the respective plurality of control instances of the entity to the respective control chemical composition, wherein the plurality of dimension reduction components of the control distribution metric is less than the plurality of features;

(c) computing the respective composite control metric, using the respective plurality of control vectors, wherein the respective control metric quantifies the on target effect of the respective set of control chemical compositions against the corresponding different gene, and wherein the control metric is computed by a third process comprising:

(1) for each respective control vector, computing a control similarity metric between (i) the respective control vector and (ii) a measure of central tendency of the respective plurality of control vectors with the respective control vector removed from the respective plurality of control vectors, thereby obtaining a plurality of control similarity metrics for the respective plurality of control vectors, each control similarity metric in the plurality of control similarity metrics uniquely corresponding to a chemical composition in the respective set of control chemical compositions, and (2) computing the respective composite control metric as a measure of central tendency of the plurality of control similarity metrics; and (D) comparing the composite test metric to the null distribution, wherein when the composite test metric is differentiated from the null distribution, the set of test chemical compositions is deemed to discriminate the on target effect against the first gene over the null distribution.

* * * * *